United States Patent [19]
Borst et al.

[11] Patent Number: 5,927,284
[45] Date of Patent: *Jul. 27, 1999

[54] METHOD AND APPARATUS FOR TEMPORARILY IMMOBILIZING A LOCAL AREA OF TISSUE

[75] Inventors: Cornelius Borst; Hendricus J. Mansvelt Beck, both of Bilthoven; Paul F. Gründeman, Amsterdam; Erik W. L. Jansen, Zeist, all of Netherlands

[73] Assignee: Medtronic, Inc, Minneapolis, Minn.

[*] Notice: This patent is subject to a terminal disclaimer.

[21] Appl. No.: 08/915,678

[22] Filed: Aug. 21, 1997

Related U.S. Application Data

[63] Continuation of application No. 08/531,363, Sep. 20, 1995.

[51] Int. Cl.$^6$ .................................................. A61F 2/00
[52] U.S. Cl. ........................... 128/898; 600/37; 600/201
[58] Field of Search ............................ 128/898; 600/37, 600/201

[56] References Cited

U.S. PATENT DOCUMENTS

| | | |
|---|---|---|
| 3,720,433 | 3/1973 | Rosfelder . |
| 3,858,926 | 1/1975 | Ottenhues . |
| 4,366,819 | 1/1983 | Kaster . |
| 4,368,736 | 1/1983 | Kaster . |
| 4,646,747 | 3/1987 | Lundback . |
| 4,736,749 | 4/1988 | Lundback . |
| 4,808,163 | 2/1989 | Laub . |
| 4,854,318 | 8/1989 | Solem et al. . |

(List continued on next page.)

FOREIGN PATENT DOCUMENTS

| | | |
|---|---|---|
| 9418881 | 9/1994 | WIPO . |
| 9501757 | 1/1995 | WIPO . |
| 9515715 | 6/1995 | WIPO . |
| 9600033 | 1/1996 | WIPO . |

OTHER PUBLICATIONS

Society of Thoracic Surgeons, 1993. Fanning et al, "Reoperative Coronary Artery Bypass Grafting Without Cardiopulmonary Bypass".

Jrnl. of The Society of Thoracic Surgeons and the Southern Thoracic Surgical Assn. vol. 19. No. 1. Jan. 1975—Trapp et al, Placement of Coronary Artery Bypass Graft Without Pump Oxygenator:.

Abstract: "Closed Chest Coronary Artery Bypass With Cardioplegic Arrest in the Dog", Stevens et al, 67th Scientific Sessions.

*Primary Examiner*—Robert L. Nasser
*Attorney, Agent, or Firm*—Harold R. Patton; Peter Forrest

[57] ABSTRACT

A method and apparatus for temporarily immobilizing a local area of tissue. In particular, the present invention provides a method and apparatus for temporarily immobilizing a local area of heart tissue to thereby permit surgery on a coronary vessel in that area without significant deterioration of the pumping function of the beating heart. The local area of heart tissue is immobilized to a degree sufficient to permit minimally invasive or micro-surgery on that area of the heart. The present invention features a suction device to accomplish the immobilization. The suction device is coupled to a source of negative pressure. The suction device has a series of suction ports on one surface. Suction through the device causes suction to be maintained at the ports. The device further is shaped to conform to the surface of the heart. Thus, when the device is placed on the surface of the heart and suction is created, the suction through the ports engages the surface of the heart. The suction device is further fixed or immobilized to a stationary object, such as an operating table or a sternal or rib retractor. Thus, the local area of the heart near the suction device is temporarily fixed or immobilized relative to the stationary object while suction is maintained. In such a fashion, the coronary artery may be immobilized even though the heart itself is still beating so that a bypass graft may be performed. In addition the suction device may be used in either a conventional, open-chest environment or in a minimally-invasive environment, e.g. endoscopic.

13 Claims, 11 Drawing Sheets

U.S. PATENT DOCUMENTS

| | | |
|---|---|---|
| 4,865,019 | 9/1989 | Phillips . |
| 4,989,587 | 2/1991 | Farley . |
| 5,011,469 | 4/1991 | Buckberg et al. . |
| 5,053,041 | 10/1991 | Ansari et al. . |
| 5,167,223 | 12/1992 | Koros et al. . |
| 5,287,861 | 2/1994 | Wilk . |
| 5,365,921 | 11/1994 | Bookwalter et al. . |
| 5,372,124 | 12/1994 | Takayama et al. . |
| 5,374,277 | 12/1994 | Hassler . |
| 5,425,705 | 6/1995 | Evard et al. . |
| 5,437,651 | 8/1995 | Todd et al. . |
| 5,472,438 | 12/1995 | Schmit et al. . |
| 5,509,890 | 4/1996 | Kazama ................................. 600/37 |
| 5,613,937 | 3/1997 | Garrison et al. ..................... 600/201 |
| 5,727,569 | 3/1998 | Benetti et al. ....................... 128/898 |
| 5,782,746 | 7/1998 | Wright .................................. 600/37 |

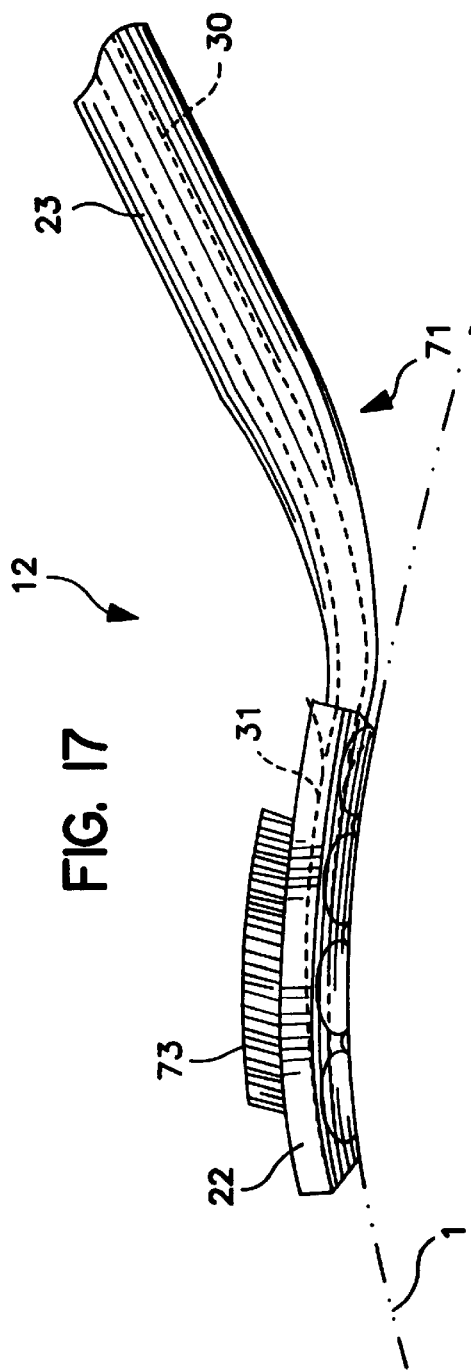
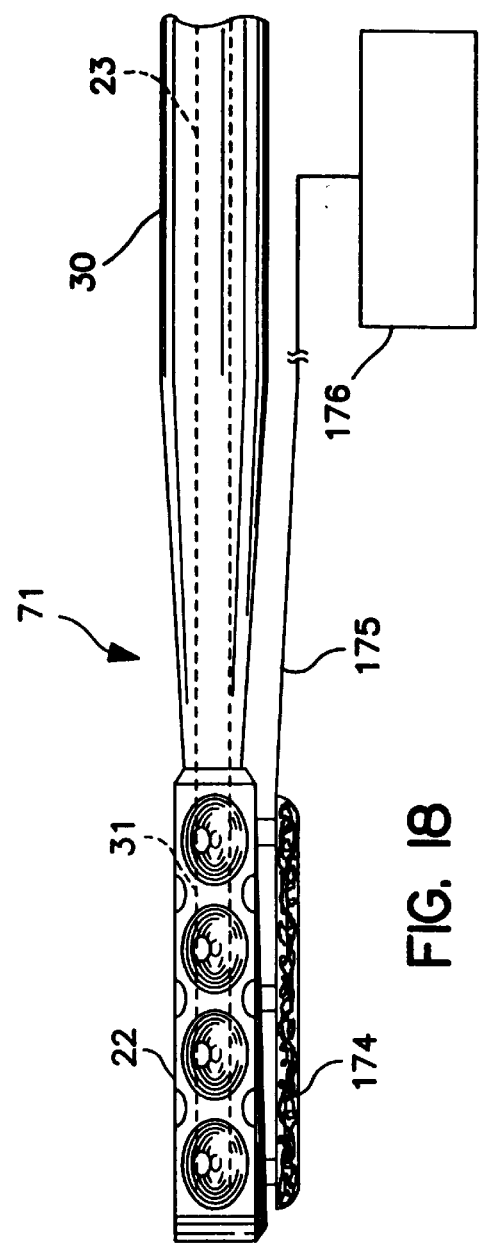

METHOD AND APPARATUS FOR TEMPORARILY IMMOBILIZING A LOCAL AREA OF TISSUE

"This application is a continuation application Ser. No. 08/531,363 filed on Sep.20, 1995

FIELD OF THE INVENTION

The present invention generally relates to surgery on body tissues and organs. More specifically, the present invention relates to a method and apparatus for temporarily immobilizing a local area of tissue subject to motion, such as the heart wall, which permits a surgical procedure to be performed on that local area of tissue.

BACKGROUND OF THE INVENTION

Coronary artery disease remains the leading cause of morbidity and mortality in Western societies. Coronary artery disease is manifested in a number of ways. For example, disease of the coronary arteries can lead to insufficient blood flow to various areas of the heart. This can lead to the discomfort of angina and the risk of ischemia. In severe cases, acute blockage of coronary blood flow can result in irreversible damage to the myocardial tissue including myocardial infarction and the risk of death.

A number of approaches have been developed for treating coronary artery disease. In less severe cases, it is often sufficient to merely treat the symptoms, with pharmaceuticals, or treat the underlying causes of the disease, with lifestyle modification. In more severe cases, the coronary blockage can be treated endovascularly or percutaneously using techniques such as balloon angioplasty, atherectomy, laser ablation, stents, and the like.

In cases where these approaches have failed or are likely to fail, it is often necessary to perform a coronary artery bypass graft procedure. This procedure generally consists of the following steps: First, direct access to the heart is achieved. This is usually done by opening the chest by median sternotomy and spreading the left and right rib cage apart; and opening the pericardial sac to achieve direct access to the heart.

Next, a blood vessel or vessels for use in the graft procedure are mobilized from the patient. This usually entails mobilizing either a mammary artery or a saphenous vein, although other graft vessels may also be used.

Next, a heart-lung or cardiopulmonary bypass is performed. This usually entails arterial and venous cannulation, connecting the bloodstream to a heart-lung machine, cooling the body to about 32 degrees Celsius, cross-clamping of the aorta and cardioplegic perfusion of the coronary arteries to arrest and cool the heart to about 4 degrees Celsius. The arrest or stoppage of the heart is generally required because the constant pumping motion of the beating heart would make surgery upon the heart difficult in some locations and extremely difficult if not impossible in other locations Once cardiac arrest is achieved, then a graft (or grafts) is attached to the relevant portions of a coronary artery (or arteries) followed by weaning from the cardiopulmonary bypass, restarting the heart and decannulation. Finally the chest is closed.

One area which may create difficulties for the patient and extra expense and time for the procedure involves the cardiopulmonary bypass. In a cardiopulmonary bypass all the patient's blood, which normally returns to the right atrium, is diverted to a system which supplies oxygen to the blood and removes carbon dioxide and returns the blood, at sufficient pressure, into the patient's aorta for further distribution into the body. Generally such a system requires several separate components, including an oxygenator, several pumps, a reservoir, a blood temperature control system, filters as well as flow, pressure and temperature sensors.

Problems may develop during cardiopulmonary bypass due to the reaction blood has to non-endothelially lined surfaces, i.e. surfaces unlike those of a blood vessel. In particular, exposure of blood to foreign surfaces results in the activation of virtually all the humoral and cellular components of the inflammatory response, as well as some of the slower reacting specific immune responses. Other complications from cardiopulmonary bypass include loss of red blood cells and platelets due to shear stress damage. In addition, cardiopulmonary bypass requires the use of an anticoagulant, such as heparin. This may, in turn, increase the risk of hemorrhage. Finally cardiopulmonary bypass sometimes necessitates giving additional blood to the patient. The additional blood, if from a source other than the patient, may expose the patient to blood born diseases.

Due to the risks incurred during cardiopulmonary bypass, others have attempted to perform a coronary artery bypass graft procedure without cardiac arrest and cardiopulmonary bypass. For example, Trapp and Bisarya in "Placement of Coronary Artery Bypass Graft Without Pump Oxygenator", Annals Thorac. Surg. Vol. 19,No.1,(January 1975) pgs.1–9, immobilized the area of the bypass graft by encircling sutures deep enough to incorporate enough muscle to suspend an area of the heart and prevent damage to the coronary artery. More recently Fanning et al. in "Reoperative Coronary Artery Bypass Grafting Without Cardiopulmonary Bypass, "Annals Thorac. Surg. Vol. 55, (Febuary 1993) pgs. 486–489 also reported immobilizing the area of the bypass graft with stabilization sutures.

While these attempts have achieved some success, they generally require enhanced skill of the surgeon to properly create the anastomsis because, even with sutures, the beating heart continues to move in the relevant area more than desired.

SUMMARY OF THE INVENTION

It is thus an object of the present invention to provide a method and apparatus for temporarily immobilizing a local area of tissue, such as an area of a beating heart, without requiring the use of stabilizing sutures.

It is a further object of the present invention to provide a method and apparatus to facilitate performing coronary artery bypass graft surgery on a beating heart.

It is the further object of the present invention to provide a method and apparatus to perform a coronary artery bypass graft without requiring the heart to be arrested or stopped and the patient coupled to a cardiopulmonary bypass machine.

These and other objectives are met by the present invention which comprises a method and apparatus for temporarily immobilizing a local area of tissue. In particular, the present invention provides a method and apparatus for temporarily immobilizing a local area of heart tissue to thereby permit surgery on a coronary vessel in that area without significant deterioration of the pumping function of the beating heart. The local area of heart tissue is immobilized to a degree sufficient to permit minimally invasive or micro-surgery on that area of the heart. The present invention features a suction device to accomplish the immobilization. The suction device is coupled to a source of negative pressure. The suction device has a series of suction ports on one surface. Suction through the device causes suction to be maintained at the ports. The device further is shaped to conform to the surface of the heart. Thus, when the device is placed on the surface of the heart and suction is created, the suction through the ports engages the surface of the heart. The suction device is further fixed or immobilized to a stationary object, such as an operating table or a sternal or rib retractor. Thus, the local area of the heart near the suction device is temporarily fixed or immobilized relative to the stationary object while suction is maintained. In such a fashion, the coronary artery may be immobilized even though the heart itself is still beating so that a bypass graft may be performed. In addition the suction device may be used in either a conventional, open-chest environment or in a minimally-invasive environment, e.g. endoscopic.

BRIEF DESCRIPTION OF THE DRAWINGS

The foregoing and other aspects of the present invention will best be appreciated with reference to the detailed description of the invention in conjunction with the accompanying drawings, wherein:

in FIG. 1.

FIG. 17 is a side view of a further alternate embodiment of the present invention, shown placed against the surface of the heart.

FIG. 18 is a bottom view of still further alternate embodiment of the present invention.

The drawings are not necessarily to scale.

DETAILED DESCRIPTION OF THE PREFERRED EMBODIMENT

Figure 1:
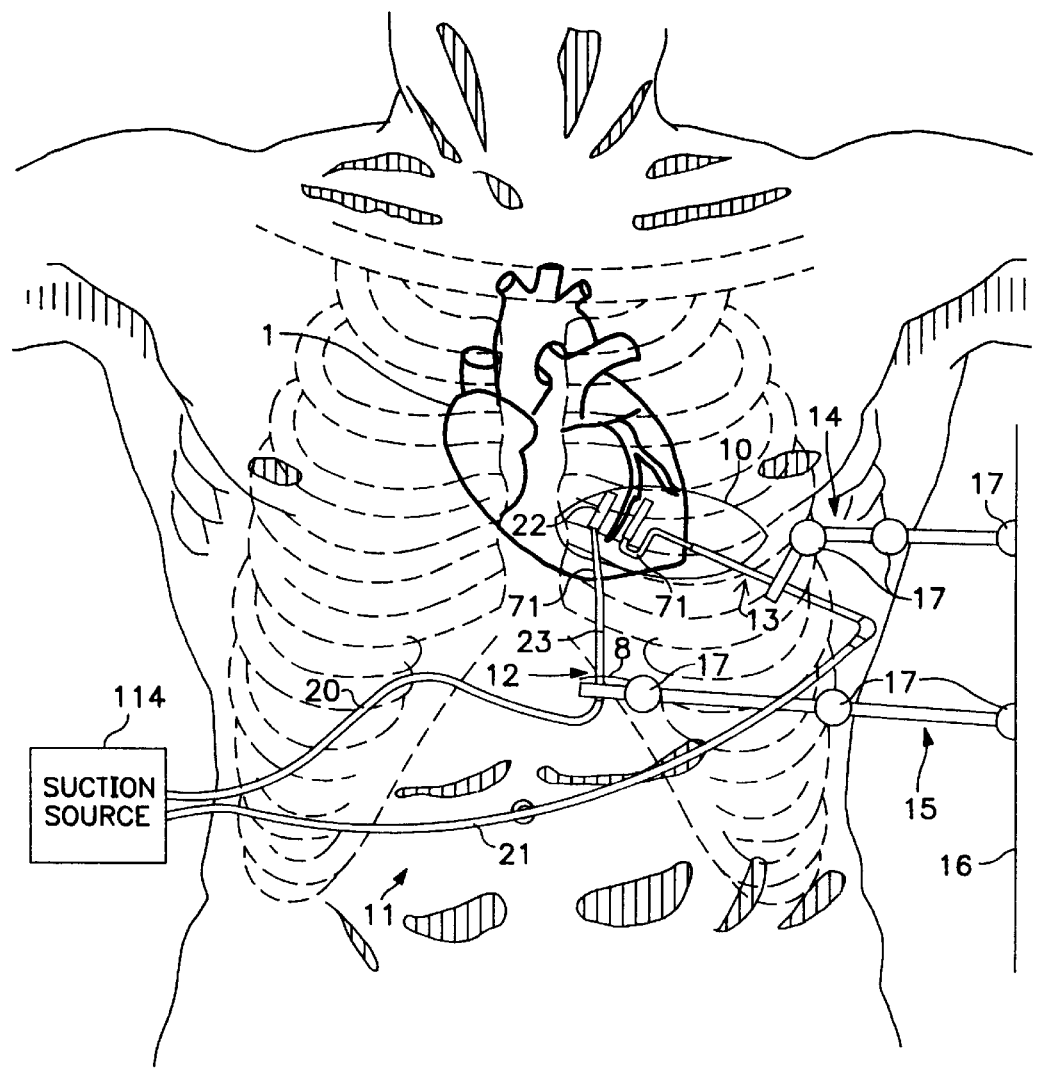
FIG. 1 is a plan view of the device being used to temporarily immobilize a local area of heart tissue in which access to the heart is achieved through a mini-thoracotomy.

FIG. 1 is a view of the immobilizing device 11 being used to temporarily immobilize an area of heart tissue. In the preferred embodiment, surgical access to the local area of heart tissue is achieved through a mini-thoracotomy, preferably performed within either the fourth or fifth intercostal space. An incision 10 of approximately 10 centimeters is made into chest cavity between the ribs (seen here in phantom.) The rib cartilage may be temporarily removed and the ribs surrounding the incision slightly spread apart using a retractor (not shown) to provide adequate surgical access to the mammary artery and the heart. As seen, a pair of suction devices 12, 13 are introduced. The first suction device 12 is introduced through a small stab wound 8 in between the ribs approximately 10 cm. below incision 10. This stab wound is made in any acceptable manner. Incidentally, once the surgery has been completed, the stab wound may be used for the thorax drain after the closure of the chest. As discussed below with reference to FIG. 19, the suction device has a covering 180, made from latex rubber, over the distal end when it penetrates the chest wall in order to avoid blood and tissue from entering the suction ports and block suction apertures. Once suction device is introduced, covering 180 is removed and the distal end is positioned onto heart. The second suction device 13 is introduced through incision 10 onto the surface of the heart. As seen, the distal end of each suction device is ultimately positioned in the local area of heart tissue to be immobilized, i.e. on either side of a coronary artery upon which a graft is to be made.

As seen, suction devices 12, 13 are secured using securing devices 14, 15 respectively to a stationary object, such as surgical table 16. Of course other objects besides the surgical table may be used as a stationary object, including the floor, ceiling or even the patient, such as a portion of the skeletal system of the patient, e.g. the sternum. In the preferred embodiment, each securing device 14, 15 is a variable friction arm, model no. 244 available from Manfrotto Nord, Inc. of Zona Industriale di Villapaiera, I-32032 Feltre BL, Italy. Each securing device 14, 15 has a series of elbow joints 17 which may be locked in position. Thus the securing device permits the suction device to be locked into any position desired within three-dimensional space. Although not show, each securing device (or each suction device or both) may also be interconnected such that a truss type structure is created and the entire stiffness or rigidity of the immobilizing device 11 is improved.

Suction devices 12, 13 are coupled to a suction source 114 through lines 20, 21. Suction source 114 is preferably the standard suction available in the operating room and coupled to the devices with a two liter buffer flask (not shown) for each device. Suction is provided at a negative pressure of between 200–600 mm Hg with 400 mm Hg preferred. As seen, each suction device has essentially two portions, a paddle 22 and an arm 23. FIGS. 2 and 3 detail suction devices 12 and 13 respectively.

Figure 2A:
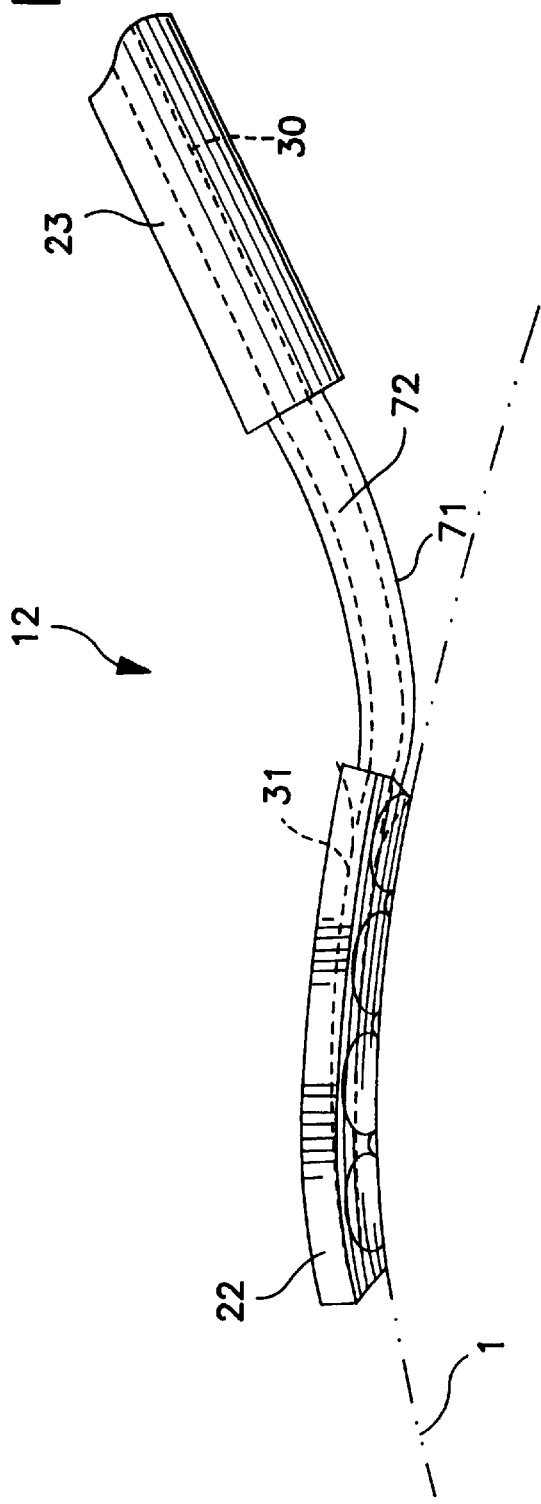
FIGS. 2a 2b depict a first type of suction device shown in use in FIG. 1.
Figure 2B:
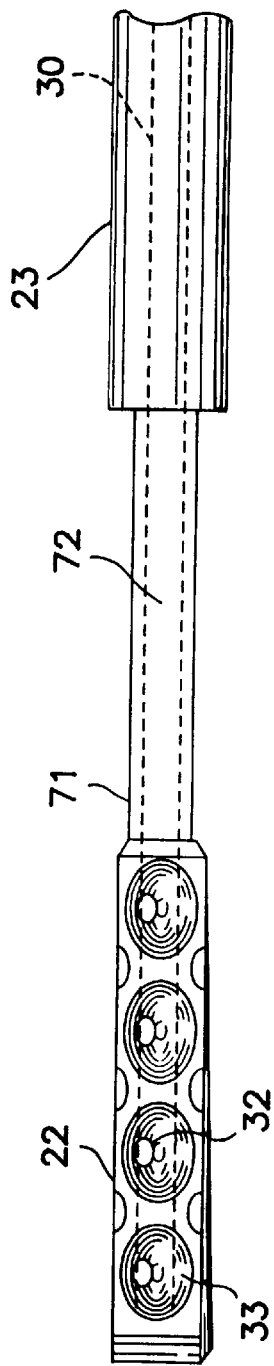

Turning now to FIGS. 2a and 2b, FIG. 2a is a side view of a suction device 12 showing its placement against the outline of a heart. As seen, the distal end of suction device comprises a paddle 22 and arm 23 coupled together by a continuous hinge or neck 71. Paddle 22 has a generally planar surface which conforms generally to the curvature of a heart 1, shown here in outline. In the preferred embodiment, suction arm 23 is coupled to suction paddle 22 such that suction paddle 22 may be rotated or bent to achieve the desired orientation relative to arm 23. This is accomplished by neck 71. Neck 71 is fashioned to be relatively bendable, that is to be bent by hand into the desired orientation, as opposed to paddle 22 and arm 23, which are rigid. In the preferred embodiment suction paddle 22 and suction arm 23 are constructed of stainless steel 316, while neck 71 is constructed of stainless steel 321. Of course other means may be provided to permit paddle 22 to move or rotate relative to arm 23 other than making neck 71 to be malleable by hand, such as a locking hinge as well as a remotely actuable joint, as is well known in the art. See for example, U.S. Pat. No. 5,374,277 of Hassler, incorporated herein by reference. A remotely actuable hinge is believed particularly advantageous for a suction device used endoscopically. In an alternate embodiment paddle may be fixed in a rigid orientation relative to arm. As seen, arm 23 has a suction lumen 30 therethrough which communicates with a suction conduit 31 in paddle 22 through neck lumen 72. Suction conduit 31 in paddle 22 further communicates through suction hole 32 (best seen in FIG. 2b) to suction port 33.

FIG. 2b is a view of the bottom of suction device 12. As seen, in the preferred embodiment four suction ports 33 in a row are featured, although the specific or exact number and position used may vary. Each suction port 33 has a suction aperture 32, each of which are preferably located at a position off center from suction port 33. Suction apertures 32 are positioned off center from suction ports 33 so that if a large upwelling of tissue is caused by the suction (which may occur as a blister or bell-shaped curve) the tissue will not immediately close off the suction by obstructing suction aperture 32, as it would if the aperture were in the center of suction port 33. In addition, each suction aperture 32 has a much smaller diameter as compared to the diameter of suction port 33. This creates a high resistance pathway between suction port 33 and suction conduit 31 which permits the loss of a tissue-to-port seal in one suction port (and thus loss of fixation of the suction port to the tissue) to not also cause a precipitous pressure drop in the remainder of the suction ports. In the preferred embodiment suction aperture 32 has a diameter of 2 mm and suction port 33 has a diameter of 6 mm.

Figure 3A:
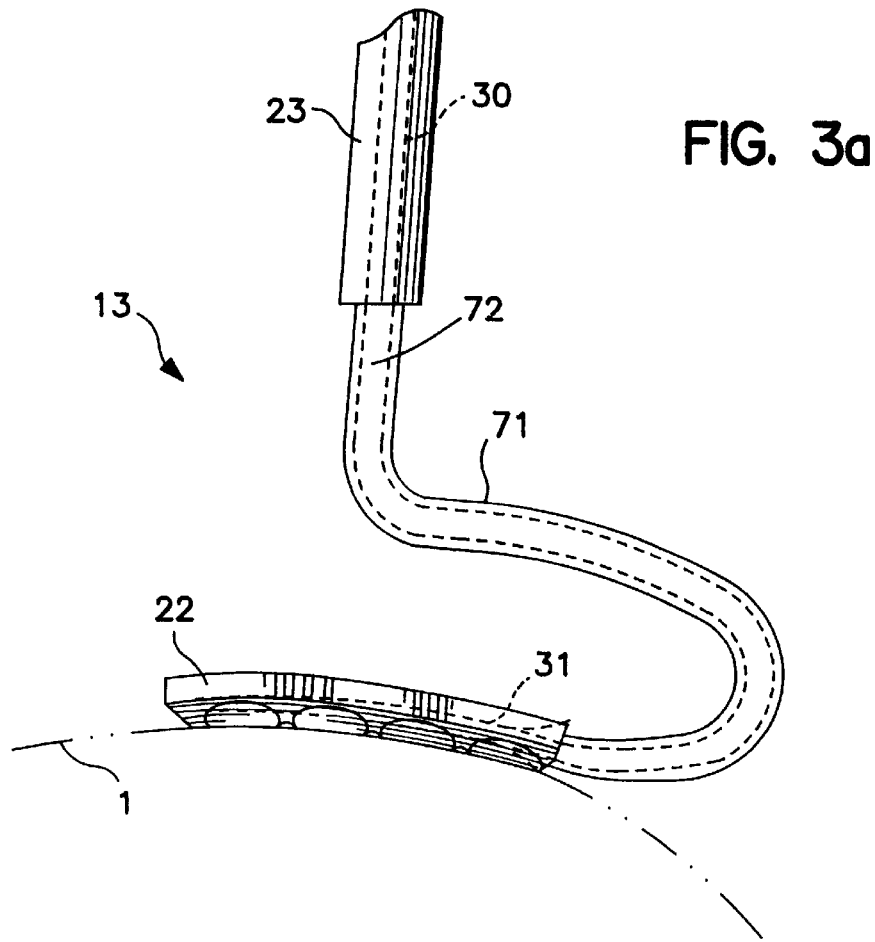
FIGS. 3a and 3b depict a second type of suction device shown in use in FIG. 1.
Figure 3B:
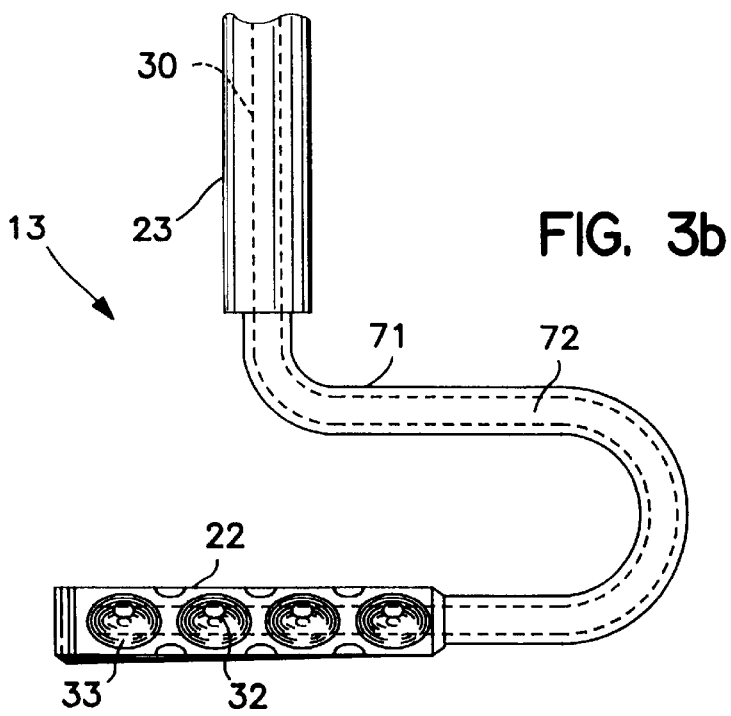

Turning now to FIGS. 3a and 3b, FIG. 3a is a side view of a suction device 13 shown in FIG. 1. As seen, the distal end of suction device 13 comprises paddle 22 and arm 23 coupled together by a continuous hinge or neck 71. Paddle 22 has a generally planar surface which conforms generally to the curvature of a heart 1. In the preferred embodiment, suction arm 23 is coupled to suction paddle 22 such that suction paddle 22 may be rotated or bent along any of the three axes to achieve the desired orientation relative to arm 23. This is accomplished by neck 71. Neck 71 is substantially similar to that discussed in FIG. 2a but for the fact that suction device 13 has suction paddle 22 at an angled orientation to suction arm 23. In the preferred embodiment suction paddle 22 of suction device 13 is perpendicular to suction arm 23, although other angular orientations may be used.

FIG. 3b is a view of the bottom of suction device 13. As seen, in the preferred embodiment suction paddle 22 of suction device 13 is substantially similar to that described in FIG. 2b. In the preferred embodiment suction aperture 32 has a diameter of 2 mm and suction port 33 has a diameter of 6 mm.

Figure 4:
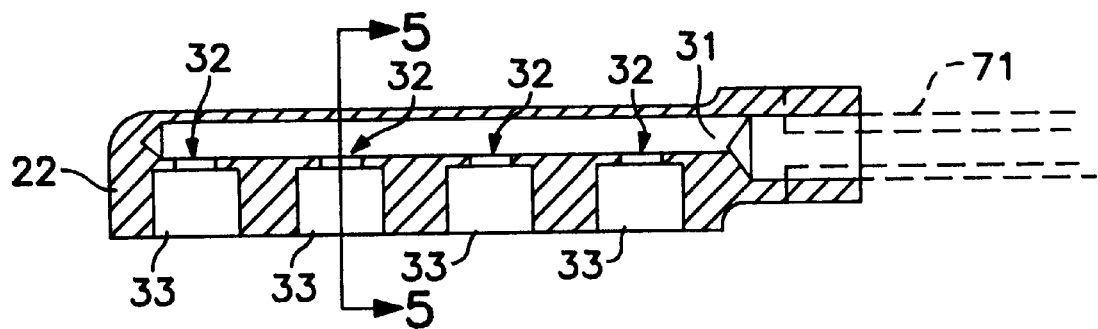
FIG. 4 is a longitudinal sectional view of the suction paddle used in the present invention.

FIG. 4 is a longitudinal cross-sectional view of suction paddle 22 used in immobilizing device 11. As seen, paddle 22 has a series of suction ports 33 each of which is connected to suction conduit 31 through a suction aperture 32. Each suction port 33 has generally straight, cylindrical sides. Of course other configurations may be used, such as cone-shaped suction ports, dome-shaped suction ports, etc.

Figure 5:
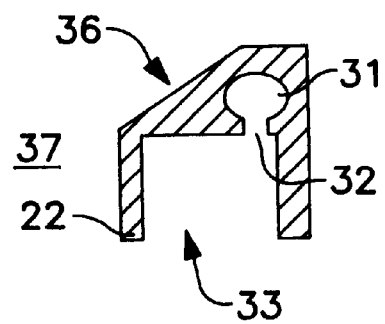
FIG. 5 is a cross-sectional view of the suction paddle used in the present invention taken along the line 5—5 of FIG. 4.

FIG. 5 is a cross-sectional view of the suction paddle 22 taken along the line 5—5 of FIG. 4. As seen, suction port 33 is connected to suction conduit 31 through suction aperture 32. Suction paddle 22 has a canted or slanted surface 36 at the top. Through this type of surface, area 37 may be better accessed for performing surgical procedures.

Figure 6:
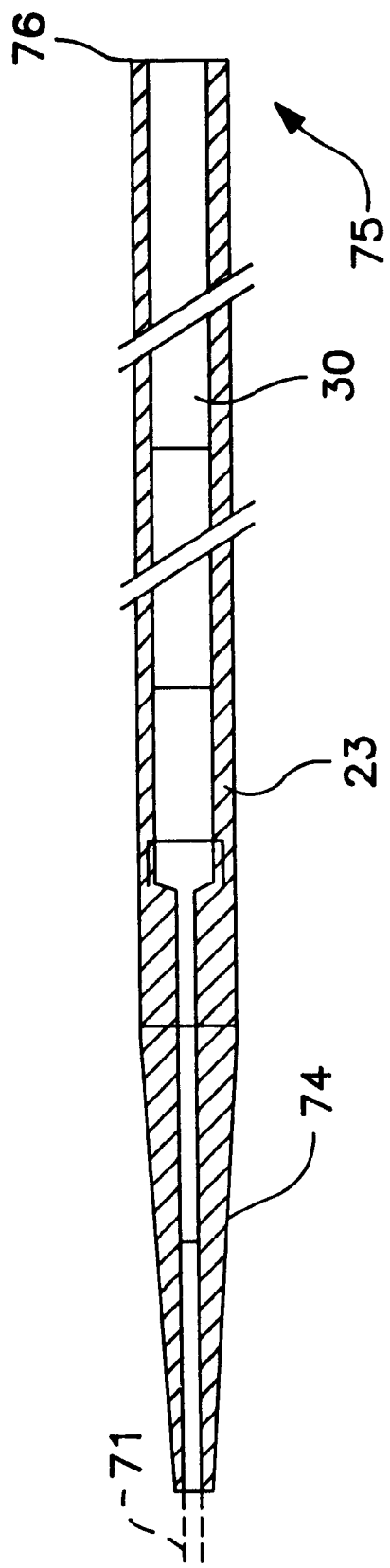
FIG. 6 is a longitudinal sectional view of the suction arm used in the present invention.
Figure 7:
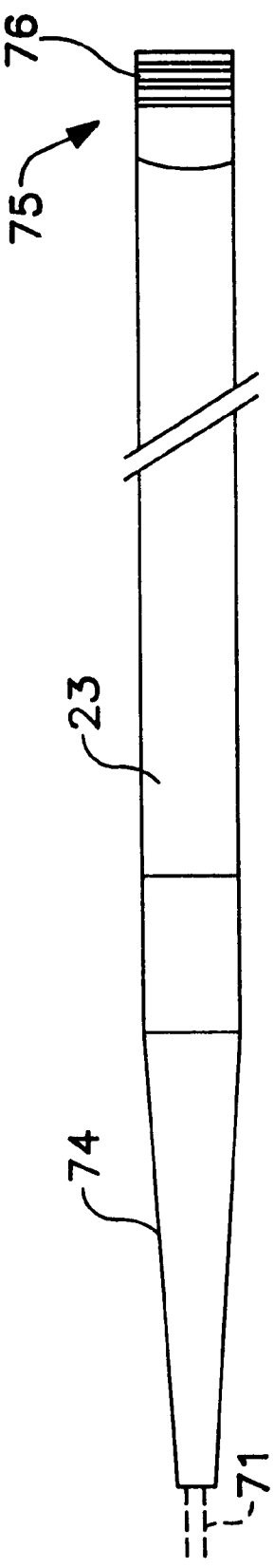
FIG. 7 is a plan view of the suction arm used in the present invention.

FIG. 6 is a longitudinal cross-sectional view of suction arm 23. Distal end 71 of suction arm 23 has neck 71 (not shown in this FIG.) fixed thereto. As seen, arm 23 has a suction lumen 30 therethrough which communicates with suction conduit 31 in paddle 22 through neck lumen 72 of neck 71 (shown in phantom in this FIG.). As seen in FIG. 7, which is a plan view of suction arm 23, proximal end 75 has a series of knurled ridges 76 to facilitate coupling a suction line coming from suction source (not shown in this FIG) to suction arm 23.

Figure 8:
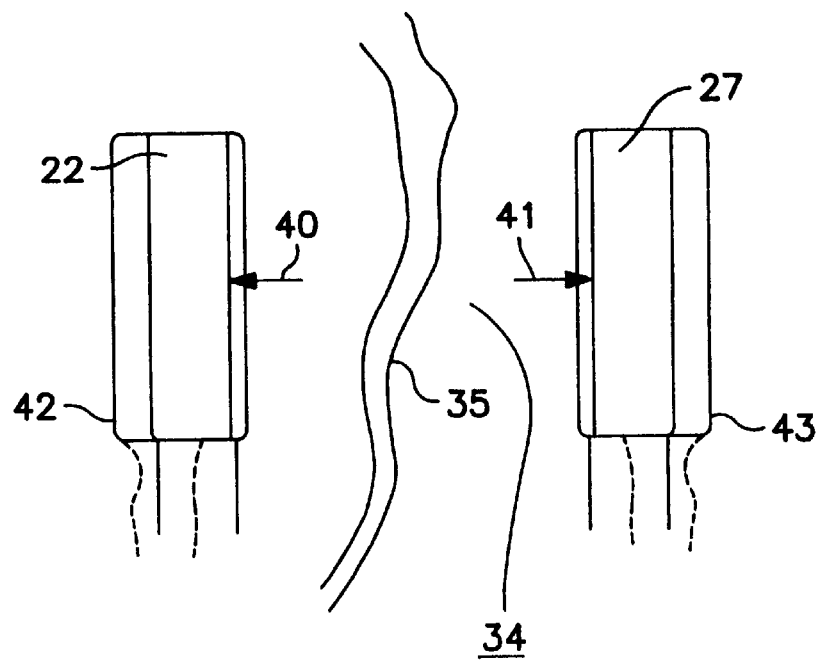
FIG. 8 is a detailed view of a pair of suction devices being positioned on a heart and spread apart.

FIG. 8 is a detailed view of a pair of suction devices 12, 13 being positioned on a heart and spread apart. As seen, paddles 22, 27 of each device generally are placed in the area 34 in which temporary immobilization of the heart tissue is desired. When used for a coronary bypass graft, area 34 typically will have a coronary artery 35 running therethrough. Area 34 is between paddles 22, 27. Once placed about area 34, suction is then created in the suction ports (not shown in this view.) Through the suction, the device then is fixed to or grabs hold of the heart tissue.

Once the suction is created and the paddles are secured to the heart tissue, each of the suction devices are then spread slightly apart as shown by the arrows 40, 41 to the positions shown as 42, 43. The effect of this spreading apart is to cause a tension to be created in the area 34 of the heart tissue between the paddles. The tension causes the area 34 to be further immobilized, and in particular in the Z-direction, i.e. in the direction normal to the plane defined by the surface of the heart. This is represented in FIGS. 9 and 10.

Figure 9:
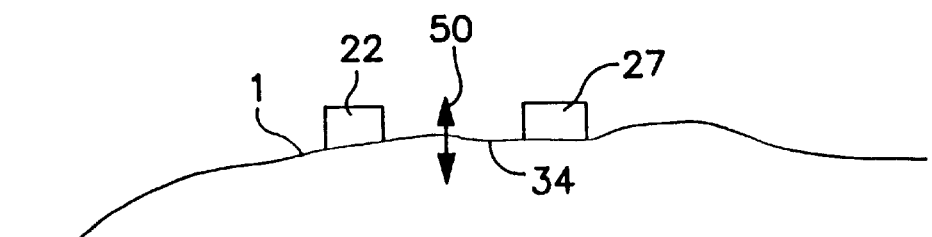
FIGS. 9 and 10 show the effect of the spread-apart motion depicted in FIG. 8.
Figure 10:
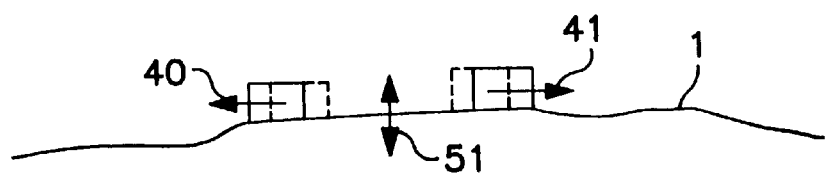

As seen in FIG. 9, the area of heart tissue between the paddles, even with the placement of the paddles, still has some vertical motion, shown here as arrow 50. When paddles 22, 27 are slightly spread apart to cause a tension in that area 34 of tissue between the paddles, as depicted in FIG. 10, then the amount of movement in the area 34 between the paddles 22, 27 due to the tension is further decreased, especially in the Z-direction, i.e. the direction perpendicular to the surface of the heart 1. Once the paddles 22, 27 are thus positioned and secured and the area of the tissue is temporarily immobilized, the coronary artery in that area may be operated upon.

In the preferred embodiment, the anastomosis of the coronary artery may be accomplished through any acceptable end-to-side or side-to-side technique. Of course, other methods of performing the anastomosis may be used, such as those methods which may be performed endoscopically.

Figure 12:
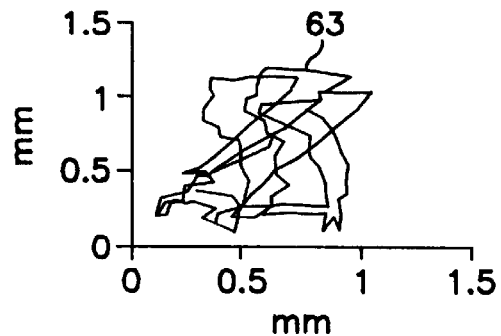
FIG. 12 is an enlarged portion of FIG. 11 depicting the motion of the same point on heart tissue when the suction devices are used.
Figure 11:
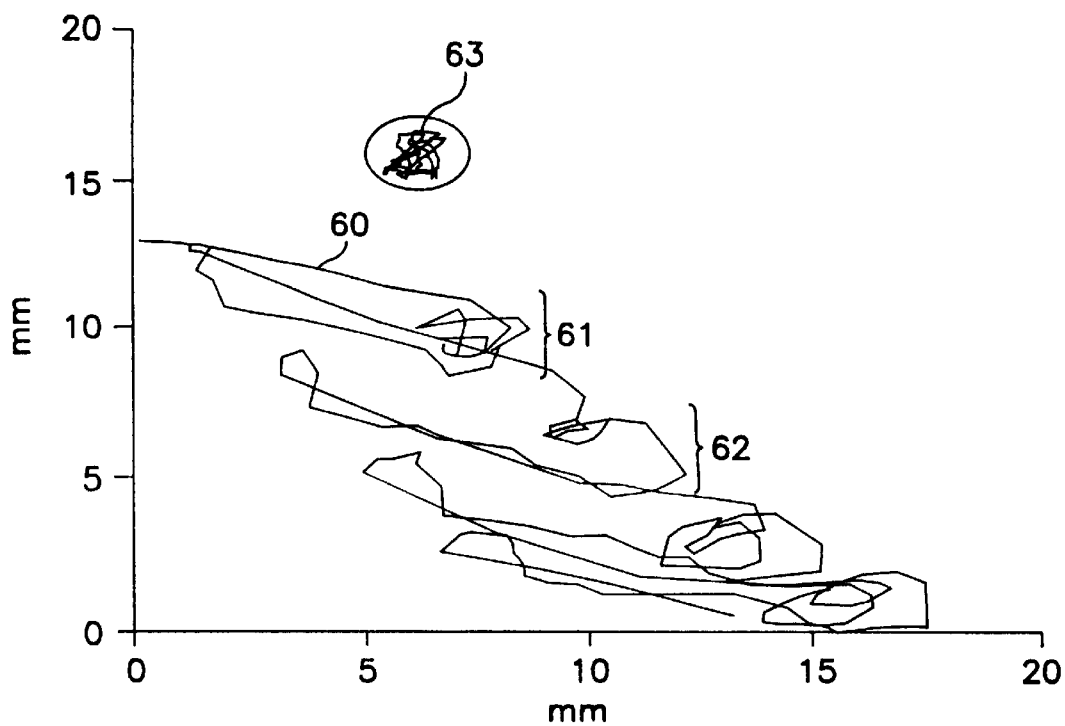
FIG. 11 is an example of the motion in the plane parallel to the surface of the heart of a point on heart tissue during one half respiratory cycle when the heart is unrestrained and also depicting the motion of the same point on heart tissue when the suction devices are used.

FIG. 11 is an example of the motion in the plane parallel to the surface of the heart of a point on heart tissue during one half respiratory cycle when the heart is unrestrained and also depicting the motion of the same point on heart tissue when the suction devices are used. Line 60 is a tracing of the motion of a point of tissue on the cardiac surface. As seen by line 60, a point on the cardiac surface moves approximately 15 mm in each direction. Generally, each loop of movement depicts the motion of the beating heart within one cardiac cycle. Thus, loop 61 occurs due to one cardiac cycle. Loop 62 occurs due to the next cardiac cycle, but the entire heart has shifted in location somewhat due to the inflation or deflation of the lungs associated with respiration. Line 63 shows the motion of the same point of heart tissue when the suction device is placed near the area and the heart wall is immobilized by the present invention. As seen, the present invention functions to minimize heart wall movement in that area to approximately 1 mm in each direction. This is best seen in FIG. 12 which is an enlarged portion of FIG. 11 and in particular line 63. As seen, through the use of the present invention, heart wall movement has been decreased to only slightly more than 1 mm. Decreased to an amount in the area of the suction devices such that the still-beating heart may be operated upon in that area using an endoscope or any other method of minimally invasive surgery.

Figure 13:
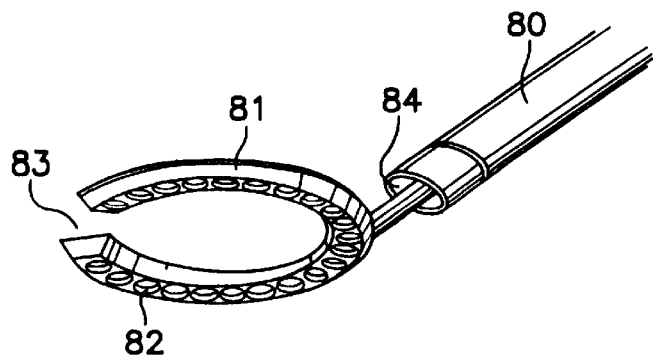
FIG. 13 is an alternate embodiment of the present invention.

FIG. 13 is an alternate embodiment of the present invention. As seen, the embodiment of FIG. 13 comprises a suction sleeve 80 which is coupled to an annular suction head 81 via a ball bearing joint 84. Ball bearing joint 84 may be provided so as to permit remote actuation of the suction head 81 from a position outside the chest. The suction head 81 has a series of suction ports 82 located along a first planar surface. In the embodiment shown the planar surface upon which the suction ports 82 are located is conical in shape, although other types of planar surface may be used, such as frusto-conical for example. The suction head 81 may be constructed such that each half of the device is coupled to a separate suction source. Through such a configuration, if one-half of the suction head 81 were to lose contact with the surface, the other one-half of the suction head 81 could maintain capture. The suction sleeve 80 is used as described above. That is the suction sleeve 80 itself is coupled to a suction source (not shown but the same as suction source 114) and is fixed or immobilized to a stationary point, such as the operating table or a retractor (also not shown.) Suction through the suction source and the suction sleeve 80 then causes the suction ports 82 to suck upon the heart tissue. Through this configuration, then, the heart tissue in the center of suction sleeve is immobilized. Interruption or opening 83 permits suction head 81 to be fixed to heart tissue while permitting a blood vessel to be grafted. In particular, if a mammary artery has been grafted end-to-side to a coronary artery, then the opening 83 permits the suction head 81 to be removed from around the grafted artery.

Figure 14:
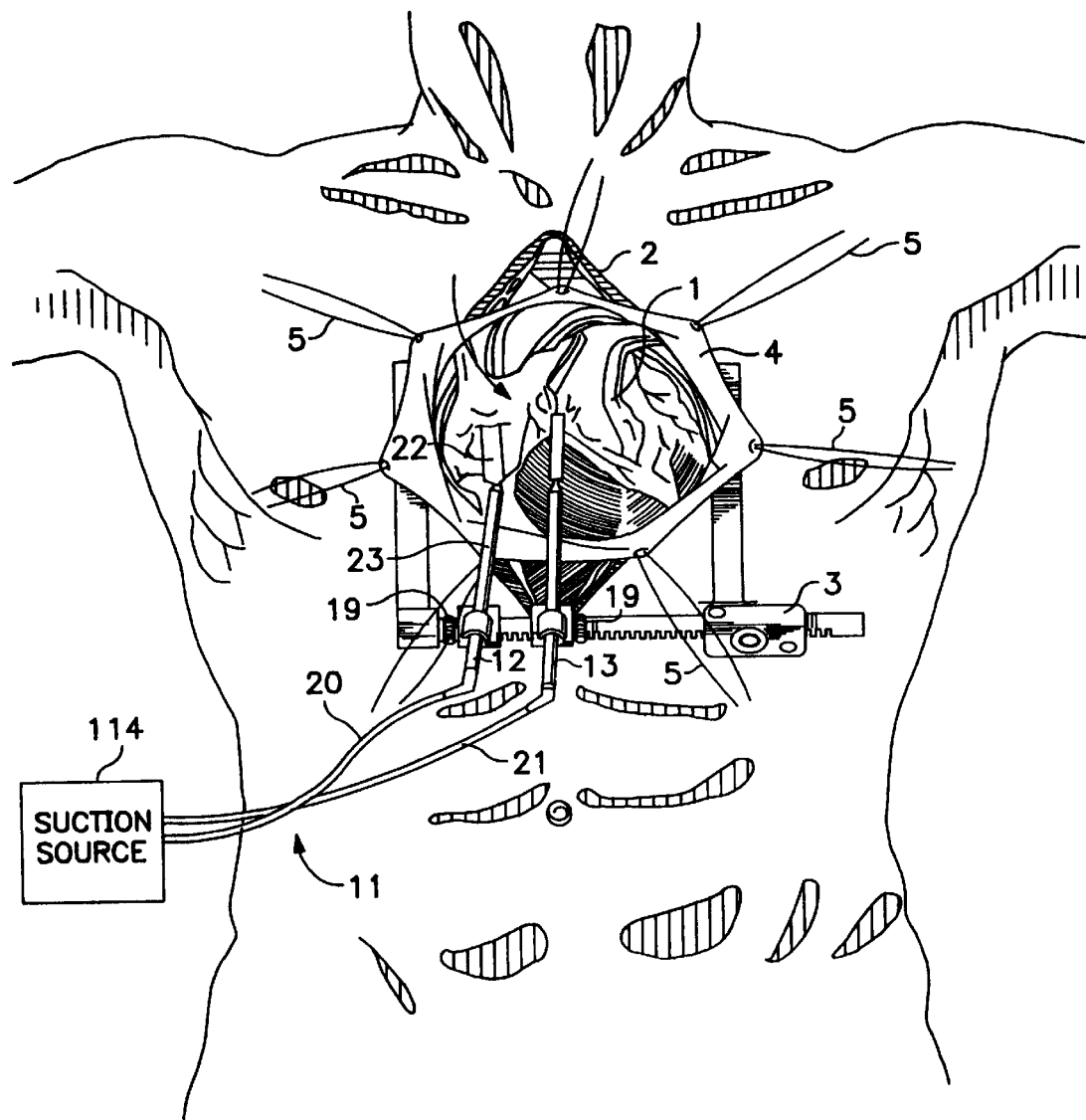
FIG. 14 is a plan view of the device being used to temporarily immobilize a local area of heart tissue in which access to the heart is achieved through a median sternotomy.

FIG. 14 is a view of the device being used to temporarily immobilize a local area of heart tissue using an alternative access procedure to the preferred mini-thoracotomy. In particular heart 1 is exposed with an incision 2 through the patient's sternum and the chest is spread apart by a retractor 3 to provide access to the heart 1. Access to the heart 1 is further effected by retraction of the pericardium 4 in the area of the heart 1 which is to be operated on. As shown pericardial retraction is accomplished through sutures 5.

As seen, the immobilizing device 11 comprises a pair of suction devices 12, 13 and a suction source 114. Suction devices 12, 13 are secured to patient be securing each to retractor 3 through a pair of clamps 19. Of course suction devices 12, 13 may also be secured to the operating table (not shown in this FIG. but using a securing device as described above. ) Suction devices are coupled to suction source 114 through lines 20, 21. Suction source 114 is preferably the standard suction available in the operating room and coupled to the devices with a two liter buffer flask (not shown) for each device. Suction is provided at a negative pressure of between 200–600 mm Hg with 400 mm Hg preferred. As seen, each suction device has essentially two portions, a paddle 22 and an arm 23.

Figure 15:
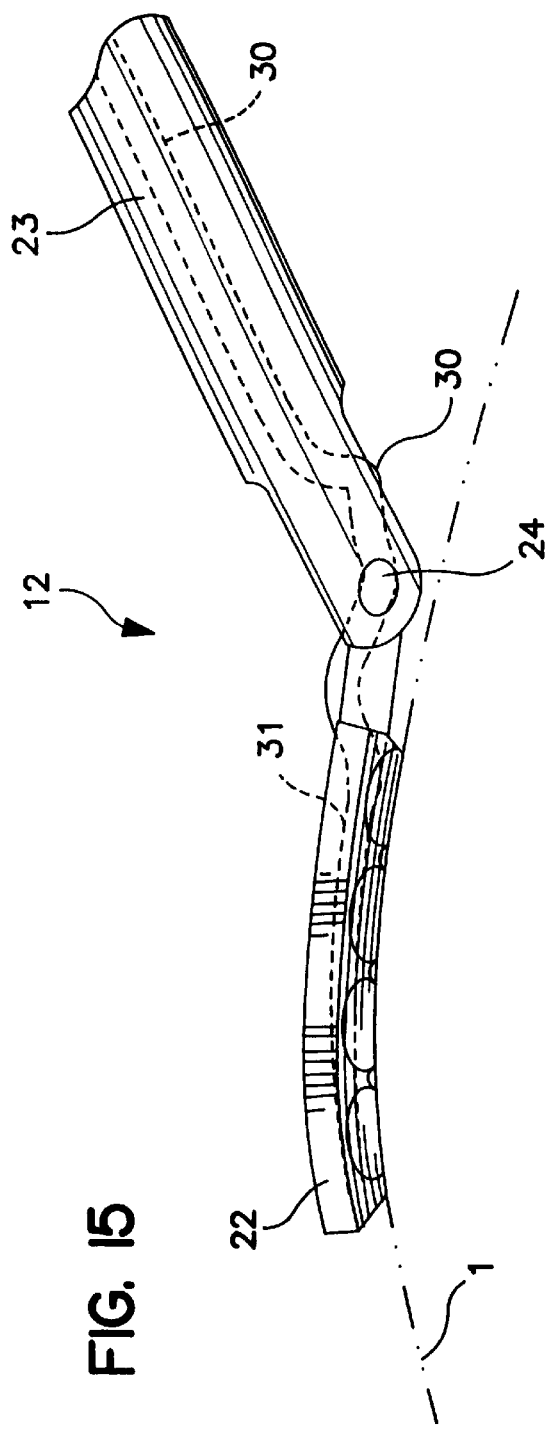
FIG. 15 is a side view of an alternate embodiment of the present invention, shown placed against the surface of the heart.

Turning now to FIG. 15 which is a side view of an alternate embodiment of suction device 12 showing its placement against the outline of a heart. As seen, the distal end of suction device comprises a paddle 22 and arm 23. Paddle 22 has a generally planar surface which conforms generally to the curvature of a heart 1, shown here in outline. The paddle 22 is coupled to arm 23 through a pin 24. The pin 24 permits the paddle 22 to be swiveled to the preferred angle relative to arm 23. As seen, arm 23 has a suction lumen 30 therethrough which communicates with a suction conduit 31 in paddle 22. Suction conduit 31, in turn, communicates through suction aperture 32 (best seen in FIG. 4) to suction port 33.

Figure 16:
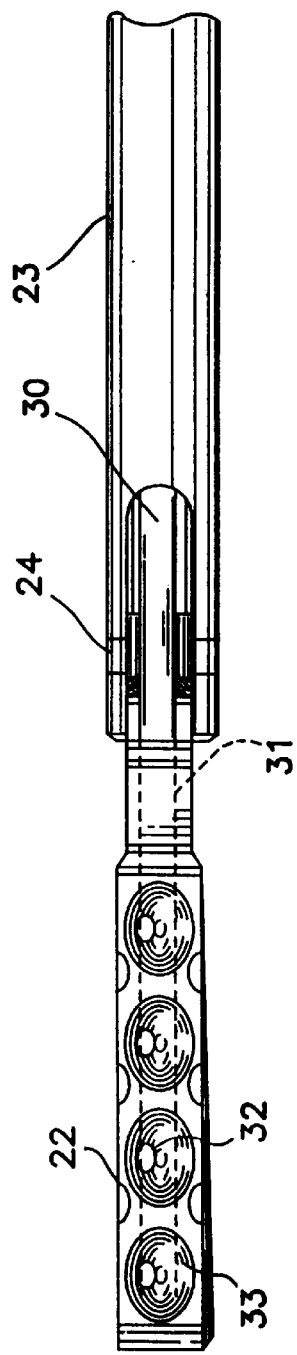
FIG. 16 is a bottom view of the alternate embodiment of the present invention device shown in FIG. 15.

FIG. 16 is a view of the bottom of suction device 12 shown in FIG. 15. As seen, four suction ports 33 in a row are featured, although the specific or exact number and position used may vary.

FIG. 17 is a further alternate embodiment of a suction device 12 showing its placement against the outline of a heart. As seen, suction device 12 is substantially similar to that shown and described in FIG. 2, but for the addition of suture coil 73. Suture coil 73 is a tightly wound spring fixed to the top surface of suction paddle 22. Further temporary stabilization of the coronary anastomosis site may be achieved, if desired, by catching epicardial flaps with light traction sutures. Suture coil 73 permits these and any other sutures to be temporarily fixed in place by wedging the suture between within suture coil 73, as is known in the art.

FIG. 18 is a bottom view of a further alternate embodiment of suction device 12. As seen, suction device 12 is substantially similar to that shown and described in FIG. 2, but for the addition of electrode 174 along a side of suction paddle 22. Electrode 174 is coupled by lead 175 to pulse generator 176. Electrode 174, lead 175 and pulse generator 176 may be provided according to well know methods and materials so as to permit the heart to be paced, cardioverted or defibrillated while suction device 12 is fixed to the surface of the heart.

Figure 19:
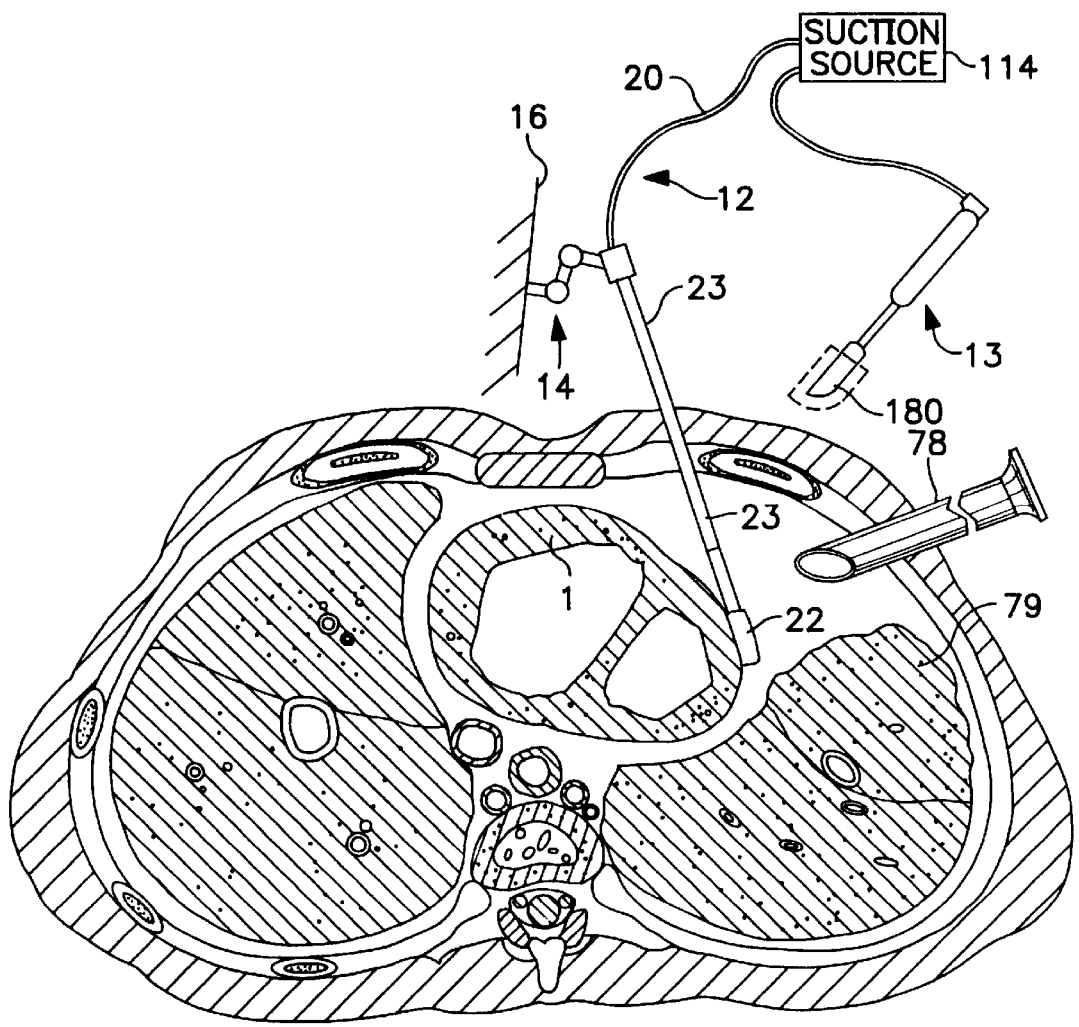
FIG. 19 is a cross-sectional view of a body showing an alternative method of achieving access to the surface of the heart, and in particular of achieving such access using minimally invasive trocars.

FIG. 19 is a cross-sectional view of a body showing an alternate method of achieving access to a surface of the heart and using the present invention to immobilize an area of tissue. As seen suction device 12 is introduced through a first stab wound. As discussed above, suction arm 23 of device 12 is secured by securing device 14 to a stationary object, such as operating table 16. A second suction device may also be introduced through a second stab wound to securely immobilize a local area of tissue. Each suction device has a covering 180, made from latex rubber, over the distal end when it penetrates the chest wall in order to avoid blood and tissue from entering the suction ports and block suction apertures. Two or more additional surgical trocars 78 may be introduced to permit endoscopy and surgical access to heart 1. In addition the left lung 79 may also be partially collapsed so as to provide an unencumbered area in which to manipulate the surgical instruments.

As disclosed, the present invention relates to a method and apparatus for immobilizing tissue. In the preferred embodiment, the invention is used to immobilize heart tissue for a coronary artery bypass graft procedure using either an open or closed chest approach, without the need for a cardiopulmonary bypass. Other surgical techniques, however, which require immobilizing body tissue may also be performed using the present invention, such as surgery on other organs such as the stomach, gall bladder, etc., as well as on other body tissues, such as the eye or the skin, for example. In addition, while the present invention has been described in detail with particular reference to a preferred embodiment and alternate embodiments, it should be understood variations and modifications can be effected within the scope of the following claims. Such modifications may include substituting elements or components which perform substantially the same function in substantially the same way to achieve substantially the same result for those described herein.

What is claimed is:

1. A method of immobilizing tissue during open or closed chest cardiac surgery comprising:

accessing a surface of the heart;

positioning a first member having at least one primary suction port on the surface of the heart;

coupling a first suction source to any primary suction port of the first member;

creating a suction with the first suction source, the created suction then communicated to any primary suction port;

grasping the surface of the heart with the suction in any primary suction port; and fixing the first member to a stationary object.

2. The method of claim 1 in which the step of accessing a surface of the heart comprises providing access through an intercostal space.

3. The method of claim 1 in which the step of accessing a surface of the heart comprises inserting an endoscope and a cutting instrument through the chest wall and cutting through the pericardium with the cutting instrument.

4. The method of claim 1 further comprising the steps of:

positioning a second member having at least one secondary suction port on the surface of the heart;

coupling the first suction source or another suction source to any secondary suction port of the second member;

grasping the surface of the heart with the suction in any secondary suction port; and fixing the second member to the stationary object.

5. The method of claim 4 further comprising the step of moving the first member away from the second member while maintaining the first member and the second member in grasping contact with the surface of the heart.

6. A method of immobilizing an area of tissue comprising:

contacting at least one primary suction port on a first paddle to a planar surface of tissue;

contacting at least one secondary suction port on a second paddle to the planar surface of the tissue;

creating a suction in at least one primary suction port to cause the first paddle to grasp the planar surface of the tissue;

creating a suction in at least one secondary suction port to cause the second paddle to grasp the planar surface of the tissue;

moving the first paddle away from the second paddle along the planar surface of the tissue; and fixing at least one of the first and second paddles to a stationary object.

7. A method of immobilizing tissue during open or closed chest cardiac surgery comprising:

accessing a surface of the heart;

positioning a first member having at least one primary suction port along a first planar surface on the surface of the heart;

coupling a first suction source to at least one primary suction port of the first member;

creating a suction with the first suction source, the created suction then communicated to at least one primary suction port;

grasping the surface of the heart with the suction in at least one primary suction port; and fixing the first member to a stationary object.

8. The method of claim 7 in which the step of accessing a surface of the heart comprises providing access through an intercostal space.

9. The method of claim 7 in which the step of accessing a surface of the heart comprises inserting an endoscope and a cutting instrument through the chest wall and cutting through the pericardium with the cutting instrument.

10. The method of claim 7 in which the step of positioning a first member having a first suction port along a first planar surface on the surface of the heart further comprises the steps of providing a first member having a first semicircular arm, the first semicircular arm having the first suction port disposed along a first planar surface of the first semicircular arm.

11. The method of claim 7 in which the step of positioning a first member having a first suction port along a first planar surface on the surface of the heart further comprises the steps of providing a first member having a first semicircular arm and a second semicircular arm, the second semicircular arm being disposed opposite the first semicircular arm to form a substantially circular area between the semicircular arms.

12. The method of claim 7 further comprising the steps of:

positioning a second member having a second suction port along a second planar surface on the surface of the heart;

coupling the first suction source or another suction source to the suction port of the second member;

grasping the surface of the heart with the suction in the second suction port; and fixing the second member to the stationary object.

13. The method of claim 10 further comprising the steps of moving the first member away from the second member while maintaining the first member and the second member in grasping contact with the surface of the heart.

* * * * *

US005927284C1

(12) EX PARTE REEXAMINATION CERTIFICATE (5274th)

United States Patent
Borst et al.

(10) Number: US 5,927,284 C1
(45) Certificate Issued: Feb. 21, 2006

(54) METHOD AND APPARATUS FOR TEMPORARILY IMMOBILIZING A LOCAL AREA OF TISSUE

(75) Inventors: Cornelius Borst, Bilthoven (NL); Hendricus J. Mansvelt Beck, Bilthoven (NL); Paul F. Gründeman, Amsterdam (NL); Erik W. L. Jansen, Zeist (NL)

(73) Assignee: Medtronic, Inc., Minneapolis, MN (US)

Reexamination Request:
No. 90/005,995, May 3, 2001

Reexamination Certificate for:
Patent No.: 5,927,284
Issued: Jul. 27, 1999
Appl. No.: 08/915,678
Filed: Aug. 21, 1997

Related U.S. Application Data

(63) Continuation of application No. 08/531,363, filed on Sep. 20, 1995, now Pat. No. 5,836,311.

(51) Int. Cl.
*A61F 2/00* (2006.01)

(52) U.S. Cl. .......................... 128/898; 600/37; 600/201
(58) Field of Classification Search ................. 128/898; 600/37, 201, 208, 215, 216, 227, 228–231, 600/235
See application file for complete search history.

(56) References Cited

U.S. PATENT DOCUMENTS

| 452,131 A | 5/1891 | Haughawout |
| 2,590,527 A | 3/1952 | Fluck |
| 3,577,982 A | 5/1971 | La Par .................... 128/2 R |

(Continued)

FOREIGN PATENT DOCUMENTS

| DE | 9004513.0 | 4/1990 |
| DE | 29708050 | 5/1997 |
| EP | 0 167 345 A1 | 1/1986 |

(Continued)

OTHER PUBLICATIONS

Kolessov V.I., *The Surgery of Coronary Arteries of the Heart*, Leningrad, Meditsina, 1977, pp 360. (Russian Article).

Kolessov V.I., *The Surgery of Coronary Arteries of the Heart*, Leningrad, Meditsina, 1977, pp 360. (English Translation).

(Continued)

*Primary Examiner*—John Lacyk

(57) ABSTRACT

A method and apparatus for temporarily immobilizing a local area of tissue. In particular, the present invention provides a method and apparatus for temporarily immobilizing a local area of heart tissue to thereby permit surgery on a coronary vessel in that area without significant deterioration of the pumping function of the beating heart. The local area of heart tissue is immobilized to a degree sufficient to permit minimally invasive or micro-surgery on that area of the heart. The present invention features a suction device to accomplish the immobilization. The suction device is coupled to a source of negative pressure. The suction device has a series of suction ports on one surface. Suction through the device causes suction to be maintained at the ports. The device further is shaped to conform to the surface of the heart. Thus, when the device is placed on the surface of the heart and suction is created, the suction through the ports engages the surface of the heart. The suction device is further fixed or immobilized to a stationary object, such as an operating table or a sternal or rib retractor. Thus, the local area of the heart near the suction device is temporarily fixed or immobilized relative to the stationary object while suction is maintained. In such a fashion, the coronary artery may be immobilized even though the heart itself is still beating so that a bypass graft may be performed. In addition the suction device may be used in either a conventional, open-chest environment or in a minimally-invasive environment, e.g. endoscopic.

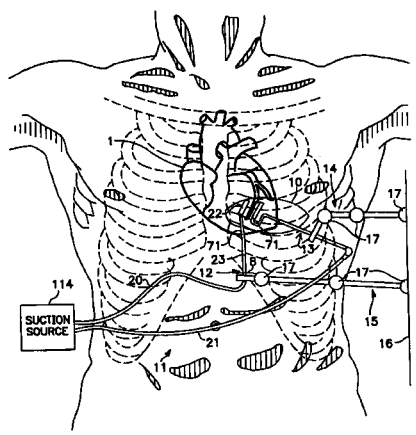

U.S. PATENT DOCUMENTS

| | | | |
|---|---|---|---|
| 3,720,433 A | 3/1973 | Rosfelder | 294/64 R |
| 3,783,873 A | 1/1974 | Jacobs | 128/303 R |
| 3,786,815 A | 1/1974 | Ericson | 128/321 |
| 3,858,926 A | 1/1975 | Ottenhues | 294/64 R |
| 3,916,909 A | 11/1975 | Kletschka et al. | 128/354 |
| 3,951,138 A | 4/1976 | Akopov | 128/17 |
| 3,983,863 A | 10/1976 | Janke et al. | 128/1 R |
| 3,999,795 A | 12/1976 | Barker | 294/64 R |
| 4,047,532 A | 9/1977 | Phillips et al. | 128/303 R |
| 4,049,000 A | 9/1977 | Williams | |
| 4,049,002 A | 9/1977 | Kletschka et al. | 128/318 |
| 4,096,864 A | 6/1978 | Kletschka et al. | 128/354 |
| 4,306,561 A | 12/1981 | De Medinaceli | 128/303.13 |
| 4,314,568 A | 2/1982 | Loving | 128/327 |
| 4,350,160 A | 9/1982 | Kolesov et al. | 128/334 R |
| 4,366,819 A | 1/1983 | Kaster | 128/334 C |
| 4,368,736 A | 1/1983 | Kaster | 128/334 C |
| 4,428,368 A | 1/1984 | Torii | |
| 4,447,227 A | 5/1984 | Kotsanis | 604/95 |
| 4,463,980 A | 8/1984 | Orii | 294/64 R |
| 4,627,421 A | 12/1986 | Symbas et al. | 128/20 |
| 4,637,377 A | 1/1987 | Loop | 128/1 R |
| 4,646,747 A | 3/1987 | Lundbáck | 128/643 |
| 4,688,570 A | 8/1987 | Kramer et al. | 128/305 |
| 4,711,247 A | 12/1987 | Fishman | 128/743 |
| 4,718,418 A | 1/1988 | L'Esperance, Jr. | 128/303.1 |
| 4,726,356 A | 2/1988 | Santilli et al. | 128/20 |
| 4,736,749 A | 4/1988 | Lundback | 128/643 |
| 4,767,142 A | 8/1988 | Takahashi et al. | 294/64.1 |
| 4,808,163 A | 2/1989 | Laub | 604/105 |
| 4,852,552 A | 8/1989 | Chaux | |
| 4,854,318 A | 8/1989 | Solem et al. | 128/346 |
| 4,863,133 A | 9/1989 | Bonnell | |
| 4,865,019 A | 9/1989 | Phillips | 128/20 |
| 4,892,343 A | 1/1990 | Hall | 294/64.1 |
| 4,904,012 A | 2/1990 | Nishiguchi et al. | 294/64 |
| 4,925,443 A | 5/1990 | Heilman et al. | 600/16 |
| 4,955,896 A | 9/1990 | Freeman | 606/210 |
| 4,962,758 A | 10/1990 | Lasner et al. | 128/41 |
| 4,973,300 A | 11/1990 | Wright | 600/37 |
| 4,989,587 A | 2/1991 | Farley | 128/20 |
| 4,991,578 A | 2/1991 | Cohen | 128/419 D |
| 5,009,660 A | 4/1991 | Clapham | 606/166 |
| 5,011,469 A | 4/1991 | Buckberg et al. | 604/4 |
| 5,053,041 A | 10/1991 | Ansari et al. | 606/148 |
| 5,098,369 A | 3/1992 | Heilman et al. | 600/16 |
| 5,108,412 A | 4/1992 | Krumeich et al. | 606/166 |
| 5,119,804 A | 6/1992 | Anstadt | 128/64 |
| 5,131,905 A | 7/1992 | Grooters | 600/16 |
| 5,133,737 A | 7/1992 | Grismer | 606/205 |
| 5,167,223 A | 12/1992 | Koros et al. | 128/20 |
| 5,171,254 A | 12/1992 | Sher | 606/166 |
| 5,207,467 A | 5/1993 | Smith | 294/64.1 |
| 5,287,861 A | 2/1994 | Wilk | 128/898 |
| 5,290,082 A | 3/1994 | Palmer et al. | 294/64.1 |
| 5,300,087 A | 4/1994 | Knoepfler | 606/207 |
| 5,324,087 A | 6/1994 | Shimose et al. | 294/64.1 |
| 5,336,252 A | 8/1994 | Cohen | 607/119 |
| 5,365,921 A | 11/1994 | Bookwalter et al. | 128/20 |
| 5,372,124 A | 12/1994 | Takayama et al. | 128/4 |
| 5,374,277 A | 12/1994 | Hassler | 606/207 |
| 5,383,840 A | 1/1995 | Heilman et al. | 600/17 |
| 5,417,709 A | 5/1995 | Slater | 606/205 |
| 5,425,705 A | 6/1995 | Evard et al. | 604/28 |
| 5,437,651 A | 8/1995 | Todd et al. | 604/313 |
| 5,452,733 A | 9/1995 | Sterman et al. | 128/898 |
| 5,472,438 A | 12/1995 | Schmit et al. | 606/1 |
| 5,503,617 A | 4/1996 | Jako | |
| 5,509,890 A | 4/1996 | Kazama | 600/37 |
| 5,545,123 A | 8/1996 | Ortiz et al. | 600/235 |
| 5,556,147 A | 9/1996 | Somekh et al. | 294/64.1 |
| 5,607,421 A | 3/1997 | Jeevanandam et al. | 606/15 |
| 5,613,937 A | 3/1997 | Garrison et al. | 600/201 |
| 5,667,624 A | 9/1997 | Akimoto et al. | 156/389 |
| 5,702,420 A | 12/1997 | Sterling et al. | 606/205 |
| 5,727,569 A | 3/1998 | Benetti et al. | 128/898 |
| 5,730,757 A | 3/1998 | Benetti et al. | |
| 5,749,892 A | 5/1998 | Vierra et al. | 600/204 |
| 5,772,583 A | 6/1998 | Wright et al. | |
| 5,782,746 A | 7/1998 | Wright | 600/37 |
| 5,799,661 A | 9/1998 | Boyd et al. | 128/898 |
| 5,807,243 A | 9/1998 | Vierra et al. | 600/204 |
| 5,827,216 A | 10/1998 | Igo et al. | 604/21 |
| 5,836,311 A | 11/1998 | Borst et al. | 128/897 |
| 5,875,782 A | 3/1999 | Ferrari et al. | 128/898 |
| 5,888,247 A | 3/1999 | Benetti | |
| 5,894,843 A | 4/1999 | Benetti et al. | 128/898 |
| 5,906,607 A | 5/1999 | Taylor et al. | 606/1 |
| 5,927,284 A | 7/1999 | Borst et al. | 128/898 |
| 5,947,896 A | 9/1999 | Sherts et al. | |
| 5,976,171 A | 11/1999 | Taylor | |
| 6,015,378 A | 1/2000 | Borst et al. | 600/37 |
| 6,017,304 A | 1/2000 | Vierra et al. | |
| 6,019,722 A | 2/2000 | Spence et al. | 600/210 |
| 6,032,672 A | 3/2000 | Taylor | 128/898 |
| 6,050,266 A | 4/2000 | Benetti et al. | |
| 6,063,021 A | 5/2000 | Hossain et al. | 600/37 |
| 6,071,235 A | 6/2000 | Furnish et al. | 600/235 |
| 6,110,187 A | 8/2000 | Donlon | 606/151 |
| 6,139,492 A | 10/2000 | Vierra et al. | 600/204 |

FOREIGN PATENT DOCUMENTS

| | | |
|---|---|---|
| EP | 0 293 760 A3 | 5/1988 |
| EP | 0 432 560 A2 | 11/1990 |
| EP | 0 630 629 A1 | 12/1994 |
| EP | 0 668 058 A1 | 8/1995 |
| EP | 0 808 606 A1 | 11/1997 |
| EP | 0 920 835 A1 | 6/1999 |
| GB | 2 140 695 A | 12/1984 |
| GB | 2 214 428 A | 9/1989 |
| GB | 2 233 561 | 1/1991 |
| GB | 2 214 428 B | 6/1991 |
| GB | 2267827 | 12/1993 |
| WO | WO 87/04081 | 7/1987 |
| WO | WO 88/00481 | 1/1988 |
| WO | WO 98/17182 | 4/1988 |
| WO | WO 94/03142 | 2/1994 |
| WO | WO 94/14383 | 7/1994 |
| WO | WO 94/14715 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | WO 98/10705 | 3/1998 |
| WO | WO 98/27869 | 7/1998 |
| WO | WO 99/16367 | 4/1999 |

OTHER PUBLICATIONS

Mammary Artery–Coronary Artery Anastomosis as Method of Treatment for Angina Pectoris, V.I Kolessov, MD/Thoracic and Cardiovascular Surgery, vol. 54, No. 4, Oct. 1967 pp 535–544.

Direct Myocardial Revascularization by Saphenous Vein Graft, R.G. Favaloro, MD; DG Effler, MD; LK Groves, MD; WG Sheldon, MD; and FM Sones, Jr., MD/The Annals of Thoracic Surgery, vol. 10, No. 2, Aug. 1970.

A Simple Technique and Device To Provide a Bloodless Operative Field in Coronary Artery Surgery Without Cross–Clamping the Aorta, M. Riahi, RJ Schlosser and LA Tomastis/The Journal of Thoracic and Cardiovascular Surgery, vol. 66, No. 6, Dec. 1973, pp. 974–978.

To Use or Not To Use the Pump Oxygenator in Coronary Bypass Operations, Drs. WG Trapp and R. Bisarya/The Annals of Thoracic Surgery, vol. 19, No. 1, Jan. 1975, pp. 108–109.

A Prospective Evaluation of the Pulsatile Assist Device, GL Zumbro, Jr., MD; G Shearer, CCP; ME Fishback, MD; and RF Galloway, MD/The Annals of Thoracic Surgery, vol. 28, No. 2 Aug. 1979, pp. 269–273.

Preservation of Interventricular Septal Function in Patients Having Coronary Artery Bypass Grafts Without Cardiopulmonary Bypass, CW Akins, MD; CA Boucher, MD; and GM Pohost, MD/American Heart Journal, vol. 107, No. 2, Feb. 1984, pp. 304–309.

Coronary Artery Revascularization Without Cardiopulmonary Bypass, R. Archer, DO; DA Ott, MD; R. Parravicini, MD; DA Cooley, MD; GJ Reul, MD; OH Frazier, MD; JM Duncan, MD; JJ Livesay, MD and WE Walker, MD, Texas Heart Institute Journal, vol. 11, No. 1, Mar. 1984, pp. 52–57.

Direct Myocardial Revascularization Without Cardiopulmonary Bypass, E. Buffolo; JCS Andrade, J Succi; LEV Leao; and C Gallucci. Thoac. Cardiovasc. Surgeon, 33 (1985) pp. 26–29.

Direct Coronary Surgery with Saphenous Vein Bypass Without Eigher Cardiopulmonary Bypass or Cardiac Arrest, FJ Benetti, The Journal of Cardiovascular Surgery, vol. 26, No. 3, May–Jun. 1985, pp. 217–222.

Heart–Mechanical Assist Device Interaction, JY Kresh; PLM Kerkhof; SM Goldman; and SK Brockman, Trans. Am. Soc. Artif. Intern. Organs, vol. XXXII, 1986, pp. 437–443.

Delayed Recovery of Severaly 'Stunned' Myocardium with the Support of a Left Ventricular Assist Device after Coronary Artery Bypass Graft Surgery, CM Ballantyne MD; MS verani, MD, FACC; HD Short, MD; C Hyatt, BSN, RN; GP Noon, MD, FACC, Journal of the American College of Cardiology, vol. 10, No. 3, Sep. 1987, pp. 710–712.

Long–Term Follow–up of Survivors of Postcardiotomy Circulatory Support, SA Ruzevich; KR Kanter; DG Pennington; MT Swartz; LR McBride; and DT Termuhlen, Trans. Am. Soc. Artif. Intern. Organs, vol. XXXIV, 1988, pp. 116–124.

Extended Clinical Support with an Implantable Left Ventricular Assist Device, MD McGee; SM Parnis; T Nakatani; T Myers; K Dasse; WD Hare; JM Duncan; VL Poirier; and OH Frazier, Trans Am. Soc. Artif. Intern. Organs, vol. XXXV, 1989, pp. 614–616.

Current Status of Cardiac Surgery: A 40–Year Review, WE Richenbacher, MD; JL Myers, MD, FACC; JA Walhausen, MD, FACC, Journal of American College of Cardiology, vol. 14, No. 3, Sep. 1989, pp. 535–544.

Transfemoral Placement of the Left Ventricular Assist Device "Hemopump" During Mechanical Resuscitation, KH Scholz; U Tebbe; M Chemnitius; H Kreuzer; T Schroder; JP Hering; P Uhlig; G Hellige; HJ Grone; R Autschbach; B Schorn; W Ruschewski; and H Dalichau, Thoracic and Cardiovascular Surgeon, vol. 38 (1990) pp. 69–72.

Direct Mechanical Ventricular Actuation for Cardiac Arrest in Humans, MP Anstadt, MD; RL Bartlett, MD; JP Malone, MD, FCCP; and GL Anstadt, VMD; Chest, vol. 100, No. 1, Jul. 1991.

Direct Myocardial Revascularization Without Extracorpoeal Circulation, FJ Benetti, MD; G Naselli, MD; M Wood, MD; and L Geffner, MD, Chest, vol. 100. No. 2, Aug. 1991, pp. 312–316.

Coronary Artery Bypass Without Cardiopulmonary Bypass, Pfister et al, The Annals of Thoracic Surgery, vol. 54 #6 Dec. 1992 pp. 1085–1092.

Coronary Artery Operation Supported by the Hemopump: An Experimental Study on Pig, U Lonn, MD; B Peterzen, MD; H Granfeldt, MD; and H Casimir–Ahn, MD, Ph.D. The Annals of Thoracic Surgery, vol. 58, No. 1, Jul. 1994, pp. 516–523.

Regional Cardiac Wall Immobilization for Open Chest and Closed Chest Coronary Artery Bypass Grafting on the Beating Heart: The 'Octopus' Method, Circulation, vol. 92. No. 8 Supplement 1, I–177 (Oct. 5, 1995).

A Minimally Invasive Surgical Method for Coronary Revascularization—Preliminary Experience in Five Patients, MC Robinson, DR Gross, and W Zeman, Circulation, (Oct. 15, 1995) vol. 92, No. 8, I–176.

Coronary Artery Bypass Grafting Without Cardiopulmonary Bypass and Without Interruption of Native Coronary Flow Using a Novel Astamosis Site Restraining Device ("Octopus"), C. Borst et al., Journal of the American College of Cardiology, vol. 27, No. 6, 1356–1364 (May 1996).

Cardiogenic Shock Complicating Acute Myocardial Infarction: the Use of Coronary Angioplasty and the Integration of the New Support Device into Patient Management, GM Gacioch, MD; Stephen G. Ellism, MD, FACC; L Lee, MD; ER Bates, MD, FACC; M Kirsh, MD, FAC; JA Walton, MD, FACC; EH Topol, MD, FACC, Journal of the American College of Cardiology, vol. 19, No. 3, Mar. 1, 1992.

Reoperative Coronary Artery Bypass Grafting Without Cardiopulmonary Bypass, WJ Fanning, MD; GS Kakos, MD; and TE Williams, Jr., MD, Ph.D., The Annals of Thoracic Surgery, vol. 55, No. 2, Feb. 1993, pp. 486–489.

Enhanced Preservation of Acutely Ischemic Myocardium with Transeptal Left Ventricular Assist, JD Fonger, MD; Y Zhou, MD; H Matsuura, MD; GS Aldea, MD; and RJ Shemin, MD, The Annals of Thoracic Surgery, vol. 57, No. 3, Mar. 1994, pp. 570–575.

Transcatheter Radiofrequency Ablation of Atrial Tissue Using a Suction Catheter, Th Lavergne et al. (PACE, vol. 12, Jan. 1989, Part II, pp. 177–186.

Abstract: "Closed Chest Coronary Artery Bypass With Cardioplegic Arrest in the Dog", Stevens et al. 67th Scientific Sessions.

Placement of Coronary Artery Bypass Graft without Pump Oxygenator, Trapp et al., Journal of The Society of Thoracic Surgeons and The Southern Thoracic Surgical Assn. vol. 19. No. 7 Jan. 1975.

Experimental Videothoracoscopic Cannulation of the Left Atrial Appendix: A Feasible Rapid Approach For Initiating Left Heart Bypass? PF Gründeman; DW Meijer; JJG Bannenberg; R tukkie; and PJ Klopper, Surgical Endoscopy (1993) 7: 511–513.

A New Retractor to Aid in Coronary Artery Surgery; A.J. Delrossi, M.D. and G. M. Lemore, M.D.; The Annals of Thoracic and Cardiovascular Surgery, vol. 36 Jul. 1983 pp101–102.

Less Invasive Coronary Surgery: Consensus From the Oxford Meeting; Stephen Westaby, FRCS and Federico J. Benetti, M.D.; Annals of Thoracic Surgery, 1996, 62:924–31.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–13 are determined to be patentable as amended.

New claims 14–137 are added and determined to be patentable.

1. A method of immobilizing tissue *of a moving surface of a beating heart while the heart continues beating* during open or closed chest cardiac surgery comprising:
   accessing [a] *the* surface of the *beating* heart;
   positioning a first member having at least one primary suction port on the surface of the *beating* heart;
   coupling a first suction source to any primary suction port of the first member;
   creating a suction with the first suction source, the created suction then communicated to any primary suction port;
   grasping the surface of the *beating* heart with the suction in any primary suction port; and
   fixing the *position of the* first member *on the surface of the beating heart by an attachment of the first member* to a stationary object *as the heart continues beating*.

2. The method of claim 1 in which the step of accessing a surface of the *beating* heart comprises providing access through an intercoastal space.

3. The method of claim 1 in which the step of accessing a surface of the *beating* heart comprises inserting an endoscope and a cutting instrument through the chest wall and cutting through the pericardium with the cutting instrument.

4. The method of claim 1 further comprising the steps of:
   positioning a second member having at least one secondary suction port on the surface of the *beating* heart;
   coupling the first suction source or another suction source to any secondary suction port of the second member;
   grasping the surface of the *beating* heart with the suction in any secondary suction port; and
   fixing the *position of the* second member *on the surface of the beating heart by an attachment of the second member* to the stationary object *as the heart continues beating*.

5. The method of claim 4 further comprising the step of moving the first member away from the second member while maintaining the first member and the second member in grasping contact with the surface of the *beating* heart.

6. A method of immobilizing an area of tissue comprising:
   contacting at least one primary suction port on a first paddle to a planar surface of tissue;
   contacting at least one secondary suction port on a second paddle to the planar surface of the tissue;
   creating a suction in at least one primary suction port to cause the first paddle to grasp the planar surface of the tissue;
   creating a suction in at least one secondary suction port to cause the second paddle to grasp the planar surface of the tissue;
   moving the first paddle away from the second paddle along the planar surface of the tissue; and
   fixing *the position of* at least one of the first and second paddles *on the planar surface of the tissue by an attachment of one of the first and second paddles* to a stationary object.

7. A method of immobilizing tissue *of a moving surface of a beating heart while the heart continues beating* during open or closed chest cardiac surgery comprising:
   accessing [a] *the* surface of the heart;
   positioning a first member having at least one primary suction port along a first planar surface on the surface of the *beating* heart;
   coupling a first suction source to at least one primary suction port of the first member;
   creating a suction with the first suction source, the created suction then communicated to at least one primary suction port;
   grasping the surface of the *beating* heart with the suction in at least one primary suction port; and
   fixing the *position of the* first member *on the surface of the beating heart by an attachment of the first member* to a stationary object *as the heart continues beating*.

8. The method of claim 7 in which the step of accessing a surface of the *beating* heart comprises providing access through an intercostal space.

9. The method of claim 7 in which the step of accessing a surface of the *beating* heart comprises inserting an endoscope and a cutting instrument through the chest wall and cutting through the pericardium with the cutting instrument.

10. The method of claim 7 in which the step of positioning a first member having a first suction port along a first planar surface on the surface of the *beating* heart further comprises the steps of providing a first member having a first semicircular arm, the first semicircular arm having the first suction port disposed along a first planar surface of the first semicircular arm.

11. The method of claim 7 in which the step of positioning a first member having a first suction port along a first planar surface on the surface of the *beating* heart further comprises the steps of providing a first member having a first semicircular arm and a second semicircular arm, the second semicircular arm being disposed opposite the first semicircular arm to form a substantially circular area between the semicircular arms.

12. The method of claim 7 further comprising the steps of:
   positioning a second member having a second suction port along a second planar surface on the surface of the *beating* heart;
   coupling the first suction source or another suction source to the suction port of the second member;
   grasping the surface of the heart with the suction in the second suction port; and
   fixing the *position of the* second member *on the surface of the beating heart by an attachment of the second member* to the stationary object *as the heart continues beating*.

13. The method of claim 10 further comprising the steps of moving the first member away from the second member while maintaining the first member and the second member in grasping contact with the surface of the *beating* heart.

*14. A method of immobilizing tissue of a moving surface of a beating heart while the heart continues beating during open or closed chest cardiac surgery comprising:* accessing the surface of the beating heart;
positioning a first member having at least one primary suction port on the surface of the beating heart;
coupling a first suction source to any primary suction port of the first member;
creating a suction with the first suction source, the created suction then communicated to any primary suction port;
grasping the surface of the beating heart with the suction in any primary suction port; and
fixing the position of the first member on the surface of the beating heart by attachment of the first member to a stationary object as the heart continues beating by means of an arm extending between the first member and the stationary object.

15. The method of claim 14 in which the step of accessing a surface of the beating heart comprises providing access through an intercostal space.

16. The method of claim 14 in which the step of accessing a surface of the beating heart comprises inserting an endoscope and a cutting instrument through the chest wall and cutting through the pericardium with the cutting instrument.

17. The method of claim 14 further comprising the steps of:
positioning a second member having at least one secondary suction port on the surface of the beating heart;
coupling the first suction source or another suction source to any secondary suction port of the second member;
grasping the surface of the beating heart with the suction in any secondary suction port; and
fixing the position of the second member on the surface of the beating heart by attachment of the second member to a stationary object as the heart continues beating by means of an arm extending between the second member and the stationary object.

18. The method of claim 17 further comprising the step of moving the first member away from the second member while maintaining the first member and the second member in grasping contact with the surface of the beating heart.

19. The method of claim 14 wherein fixing the position of the first member comprises actuating at least one joint in the arm.

20. The method of claim 19 wherein actuating the joint in the arm further comprises locking the joint.

21. The method of claim 19 wherein the joint is actuated remotely from the first member.

22. The method of claim 14 wherein fixing the position of the first member comprises actuating a plurality of joints in the arm.

23. The method of claim 22 wherein the joints are actuated remotely from the first member.

24. The method of claim 14 wherein the stationary object is a retractor.

25. The method of claim 24 further comprising using the retractor to access the surface of the beating heart.

26. The method of claim 14 wherein the stationary object is a surgical table.

27. The method of immobilizing an area of tissue comprising:
contacting at least one primary suction port on a first paddle to a planar surface of tissue;
contacting at least one secondary suction port on a second paddle to the planar surface of the tissue;
creating a suction in at least one primary suction port to cause the first paddle to grasp the planar surface of the tissue;
creating a suction in at least one secondary suction port to cause the second paddle to grasp the planar surface of the tissue;
moving the first paddle away from the second paddle along the planar surface of the tissue; and
fixing the position of at least one of the first and second paddles on the surface of the tissue by attachment of at least one of the first and second paddles to a stationary object by means of an arm.

28. The method of claim 27 wherein fixing the position of one of the first and second paddles comprises actuating at least one joint in the arm.

29. The method of claim 28 wherein actuating the joint in the arm comprises locking the joint.

30. The method of claim 28 wherein the joint is actuated remotely from the first and second paddles.

31. The method of claim 27 wherein fixing the first member to a stationary object further comprises actuating a plurality of joints in the arm.

32. The method of claim 31 wherein actuating the joints in the arm comprises locking the plurality of joints.

33. The method of claim 31 wherein the joints are actuated remotely from the first and second paddles.

34. The method of claim 27 wherein the stationary object is a retractor.

35. The method of claim 27 wherein the stationary object is a surgical table.

36. A method of immobilizing tissue of a moving surface of a beating heart while the heart continues beating during open or closed chest cardiac surgery comprising:
accessing the surface of the beating heart;
positioning a first member having at least one primary suction port along a first planar surface on the surface of the beating heart;
coupling a first suction source to at least one primary suction port of the first member;
creating a suction with the first suction source, the created suction then communicated to at least one primary suction port;
grasping the surface of the beating heart with the suction in at least one primary suction port; and
fixing the position of the first member along the first planar surface of the beating heart by attachment of the first member to a stationary object as the heart continues beating by means of an arm extending between the first member and the stationary object.

37. The method of claim 36 in which the step of accessing a surface of the beating heart comprises providing access through an intercostal space.

38. The method of claim 36 in which the step of accessing a surface of the beating heart comprises inserting an endoscope and a cutting instrument through the chest wall and cutting through the pericardium with the cutting instrument.

39. The method of claim 36 in which the step of positioning a first member having a first suction port along a first planar surface on the surface of the beating heart further comprises the steps of providing a first member having a first semicircular arm, the first semicircular arm having the first suction port disposed along a first planar surface of the first semicircular arm.

40. The method of claim 36 in which the step of positioning a first member having a first suction port along a first planar surface on the surface of the beating heart further comprises the steps of providing a first member having a first semicircular arm and a second semicircular arm, the second semicircular arm being disposed opposite the first semicircular arm to form a substantially circular area between the semicircular arms.

41. The method of claim 36 further comprising the steps of:

positioning a second member having a second suction port along a second planar surface on the surface of the beating heart;

coupling the first suction source or another suction source to the suction port of the second member;

grasping the surface of the beating heart with the suction in the second suction port; and fixing the position of the second member along the second planar surface of the beating heart by attachment of the second member to a stationary object as the heart continues beating by means of an arm extending between the second member and the stationary object.

42. The method of claim 36 further comprising the steps of moving the first member away from the second member while maintaining the first member and the second member in grasping contact with the surface of the beating heart.

43. The method of claim 36 wherein fixing the position of the first member comprises actuating at least one joint in the arm.

44. The method of claim 43 wherein actuating the joint in the arm further comprises locking the joint.

45. The method of claim 43 wherein the joint is actuated remotely from the first member.

46. The method of claim 36 wherein fixing the position of the first member comprises actuating a plurality of joints in the arm.

47. The method of claim 46 wherein the joints are actuated remotely from the first member.

48. The method of claim 36 wherein the stationary object is a retractor.

49. The method of claim 48 further comprising using the retractor to access the surface of the beating heart.

50. The method of claim 36 wherein the stationary object is a surgical table.

51. A method of immobilizing tissue of a moving surface of a beating heart while the heart continues beating during open or closed chest cardiac surgery comprising:

accessing the surface of the beating heart;

positioning a first member having at least one primary suction port on the surface of the beating heart;

coupling a first suction source to any primary suction port of the first member;

creating a suction with the first suction source, the created suction then communicated to any primary suction port;

grasping the surface of the beating heart with the suction in any primary suction port; and fixing the position of the first member by attachment of the first member to a stationary object such that the movement of the tissue is no greater than about 1 mm as the heart continues beating.

52. The method of claim 51 in which the step of accessing a surface of the heart comprises providing access through an intercostal space.

53. The method of claim 51 in which the step of accessing a surface of the heart comprises inserting an endoscope and a cutting instrument through the chest wall and cutting through the pericardium with the cutting instrument.

54. The method of claim 51 further comprising the steps of:

positioning a second mebmer having at least one secondary suction port on the surface of the heart;

coupling the first suction source or another suction source to any secondary suction port of the second member;

grasping the surface of the heart with the suction in any secondary suction port; and fixing the position of the second member by attachment of the first member to a stationary object such that the movement of the immobilized tissue is no greater than about 1 mm as the heart continues beating.

55. The method of claim 54 further comprising the step of moving the first member away from the second member while maintaining the first member and the second member in grasping contact with the surface of the heart.

56. A method of immobilizing an area of tissue of a moving surface of a beating heart while the heart continues beating comprising:

contacting at least one primary suction port on a first paddle to a planar surface of tissue;

contacting at least one secondary port on a second paddle to the planar surface of the tissue;

creating a suction in at least one primary suction port to cause the first paddle to grasp the planar surface of the tissue;

creating a suction in at least one secondary suction port to cause the second paddle to grasp the planar surface of the tissue;

moving the first paddle away from the second paddle along the planar surface of the tissue; and fixing the position of at least one of the first and second paddles by attachment of at least one of the first and second paddles to a stationary object such that the movement of the tissue is no greater than about 1 mm as the heart continues beating.

57. A method of immobilizing tissue of a moving surface of a beating heart while the heart continues beating during open or closed chest cardiac surgery comprising:

accessing the surface of the heart;

positioning a first member having at least one primary suction port along a first planar surface on the surface of the heart;

coupling a first suction source to at least one primary suction port of the first member;

creating a suction with the first suction source, the created suction then communicated to at least one primary suction port;

grasping the surface of the heart with the suction in at least one primary suction port; and grasping the surface of the beating heart with the suction in any primary suction port; and fixing the position of the first member by attachment of the first member to a stationary object such that the movement of the tissue is no greater than about 1 mm as the heart continues beating.

58. The method of claim 57 in which the step of accessing a surface of the heart comprises providing access through an intercostal space.

59. The method of claim 57 in which the step of accessing a surface of the heart comprises inserting an endoscope and a cutting instrument through the chest wall and cutting through the pericardium with the cutting instrument.

60. The method of claim 57 in which the step of positioning a first member having a first suction port along a first planar surface on the surface of the heart further comprises the steps of providing a first member having a first semicircular arm, the first semicircular arm having the first suction port disposed along a first planar surface of the first semicircular arm.

61. The method of claim 57 in which the step of positioning a first member having a first suction port along a first planar surface on the surface of the heart further comprises the steps of providing a first member having a first semicircular arm and a second semicircular arm, the second semicircular arm being disposed opposite the first semicircular arm to form a substantially circular area between the semicircular arms.

62. The method of claim 57 further comprising the steps of:
    positioning a second member having a second suction port along a second planar surface on the surface of the heart;
    coupling the first suction source or another suction source to the suction port of the second member;
    grasping the surface of the heart with the suction in the second suction port; and
    fixing the position of the second member by attachment of the second member to a stationary object such that the movement of the tissue is no greater than about 1 mm as the heart continues beating.

63. The method of claim 62 further comprising the steps of moving the first member away from the second member while maintaining the first member and the second member in grasping contact with the surface of the heart.

64. A method of immobilizing tissue of a moving surface of a beating heart while the heart continues beating during open or closed chest cardiac surgery comprising:
    accessing the surface of the beating heart;
    positioning a first member having at least one primary suction port on the surface of the beating heart;
    coupling a first suction source to any primary suction port of the first member;
    creating a suction with the first suction source, the created suction then communicated to any primary suction port;
    grasping the surface of the beating heart with the suction in any primary suction port; and
    fixing the position of the first member within three-dimensional space on the surface of the beating heart by locking the first member to a stationary object as the heart continues beating.

65. The method of claim 64 in which the step of accessing a surface of the beating heart comprises providing access through an intercostal space.

66. The method of claim 64 in which the step of accessing a surface of the beating heart comprises inserting an endoscope and a cutting instrument through the chest wall and cutting through the pericardium with the cutting instrument.

67. The method of claim 64 further comprising the steps of:
    positioning a second member having at least one secondary suction port on the surface of the beating heart;
    coupling the first suction source or another suction source to any secondary suction port of the second member;
    grasping the surface of the beating heart with the suction in any secondary suction port; and
    fixing the position of the second member within three-dimensional space on the surface of the beating heart by locking the second member to a stationary object as the heart continues beating.

68. The method of claim 67 further comprising the step of moving the first member away from the second member while maintaining the first member and the second member in grasping contact with the surface of the beating heart.

69. The method of claim 64 wherein locking the first member to a stationary object comprises actuating at least one joint in an arm.

70. The method of claim 69 wherein actuating the joint in the arm further comprises locking the joint in a desired position.

71. The method of claim 69 wherein the joint is actuated remotely from the first member.

72. The method of claim 64 wherein locking the first member to a stationary object comprises actuating a plurality of joints in an arm.

73. The method of claim 72 wherein the joints are actuated remotely from the first member.

74. The method of claim 64 wherein the stationary object is a retractor.

75. The method of claim 74 further comprising using the retractor to access the surface of the beating heart.

76. The method of claim 74 wherein the stationary object is a surgical table.

77. A method of immobilizing an area of tissue of a moving surface of a beating heart while the heart continues beating comprising:
    contacting at least one primary suction port on a first paddle to a planar surface of tissue;
    contacting at least one secondary suction port on a second paddle to the planar surface of the tissue;
    creating a suction in at least one primary suction port to cause the first paddle to grasp the planar surface of the tissue;
    creating a suction in at least one secondary suction port to cause the second paddle to grasp the planar surface of the tissue;
    moving the first paddle away from the second paddle along the planar surface of the tissue; and
    fixing the position of at least one of the first and second paddles within three-dimensional space on the surface of the beating heart by locking at least one of the first and second paddles to a stationary object as the heart continues beating.

78. The method of claim 77 wherein locking at least of one of the first and second paddles to a stationary object comprises actuating at least one joint in an arm.

79. The method of claim 78 wherein actuating the joint in the arm further comprises locking the joint in a desired position.

80. The method of claim 78 wherein the joint is actuated remotely from the first and second paddles.

81. The method of claim 77 wherein locking at least one of the first and second paddles to a stationary object further comprises actuating a plurality of joints in an arm.

82. The method of claim 81 wherein actuating the joints in the arm comprises locking the plurality of joints in a desired position.

83. The method of claim 81 wherein the joints are actuated remotely from the first and second paddles.

84. The method of claim 77 wherein the stationary object is a retractor.

85. The method of claim 77 wherein the stationary object is a surgical table.

86. A method of immobilizing tissue of a moving surface of a beating heart while the heart continues beating during open or closed chest cardiac surgery comprising:
    accessing the surface of the beating heart;
    positioning a first member having at least one primary suction port along a first planar surface on the surface of the beating heart;

coupling a first suction source to at least one primary suction port of the first member;

creating a suction with the first suction source, the created suction then communicated to at least one primary suction port;

grasping the surface of the beating heart with the suction in at least one primary suction port; and fixing the position of the first member within three-dimensional space on the surface of the beating heart by locking the first member to a stationary object as the heart continues beating.

87. The method of claim 86 in which the step of accessing a surface of the beating heart comprises providing access through an intercostal space.

88. The method of claim 86 in which the step of accessing a surface of the beating heart comprises inserting an endoscope and a cutting instrument through the chest wall and cutting through the pericardium with the cutting instrument.

89. The method of claim 86 in which the step of positioning a first member having a first suction port along a first planar surface on the surface of the beating heart further comprises the steps of providing a first member having a first semicircular arm, the first semicircular arm having the first suction port disposed along a first planar surface of the first semicircular arm.

90. The method of claim 86 in which the step of positioning a first member having a first suction port along a first planar surface on the surface of the beating heart further comprises the steps of providing a first member having a first semicircular arm and a second semicircular arm, the second semicircular arm being disposed opposite the first semicircular arm to form a substantially circular area between the semicircular arms.

91. The method of claim 86 further comprising the steps of:

positioning a second member having a second suction port along a second planar surface on the surface of the beating heart;

coupling the first suction source or another suction source to the suction port of the second member;

grasping the surface of the beating heart with the suction in the second suction port; and fixing the position of the second member within three-dimensional space on the surface of the beating heart by locking the second member to a stationary object as the heart continues beating.

92. The method of claim 91 further comprising the steps of moving the first member away from the second member while maintaining the first member and the second member in grasping contact with the surface of the beating heart.

93. The method of claim 86 wherein locking the first member to a stationary object comprises actuating at least one joint in an arm.

94. The method of claim 93 wherein actuating the joint in the arm further comprises locking the joint in a desired position.

95. The method of claim 93 wherein the joint is actuated remotely from the first member.

96. The method of claim 86 wherein locking the first member to a stationary object comprises actuating a plurality of joints in an arm.

97. The method of claim 96 wherein the joints are actuated remotely from the first member.

98. The method of claim 86 wherein the stationary object is a retractor.

99. The method of claim 98 further comprising using the retractor to access the surface of the beating heart.

100. The method of claim 86 wherein the stationary object is a surgical table.

101. A method of immobilizing tissue of a moving surface of a beating heart while the heart continues beating during open or closed chest cardiac surgery comprising:

accessing a surface of the beating heart;

positioning a first member having at least one primary suction port on the surface of the beating heart;

coupling a first suction source to any primary suction port of the first member;

creating a suction with the first suction source, the created suction then communicated to any primary suction port;

grasping the surface of the beating heart with the suction in any primary suction port; and fixing the position of the first member on the surface of the beating heart by a rigid attachment of the first member to a stationary object as the heart continues beating.

102. The method of claim 101 in which the step of accessing a surface of the beating heart comprises providing access through an intercostal space.

103. The method of claim 101 in which the step of accessing a surface of the beating heart comprises inserting an endoscope and a cutting instrument through the chest wall and cutting through the pericardium with the cutting instrument.

104. The method of claim 101 further comprising the steps of:

positioning a second member having at least one secondary suction port on the surface of the beating heart;

coupling the first suction source or another suction source to any secondary suction port of the second member;

grasping the surface of the beating heart with the suction in any secondary suction port; and fixing the position of the second member on the surface of the beating heart by a rigid attachment of the second member to a stationary object as the heart continues beating.

105. The method of claim 104 further comprising the step of moving the first member away from the second member while maintaining the first member and the second member in grasping contact with the surface of the beating heart.

106. The method of claim 101 wherein fixing the position of the first member comprises actuating at least one joint in an arm.

107. The method of claim 106 wherein actuating the joint in the arm further comprises locking the joint in a desired position.

108. The method of claim 106 wherein the joint is actuated remotely from the first member.

109. The method of claim 101 wherein fixing the position of the first member comprises actuating a plurality of joints in an arm.

110. The method of claim 109 wherein the joints are actuated remotely from the first member.

111. The method of claim 101 wherein the stationary object is a retractor.

112. The method of claim 111 further comprising using the retractor to access the surface of the beating heart.

113. The method of claim 101 wherein the stationary object is a surgical table.

114. A method of immobilizing an area of tissue comprising:

contacting at least one primary suction port on a first paddle to a planar surface of tissue;

contacting at least one secondary suction port on a second paddle to the planar surface of the tissue;

creating a suction in at least one primary suction port to cause the first paddle to grasp the planar surface of the tissue;

creating a suction in at least one secondary suction port to cause the second paddle to grasp the planar surface of the tissue;

moving the first paddle away from the second paddle along the planar surface of the tissue; and fixing the position of at least one of the first and second paddles on the surface of the tissue by a rigid attachment of one of the first and second paddles to a stationary object.

115. The method of claim 114 wherein fixing the position of one of the first and second paddles comprises actuating at least one joint in an arm.

116. The method of claim 115 wherein actuating the joint in the arm further comprises locking the joint in a desired position.

117. The method of claim 115 wherein the joint is actuated remotely from the first and second paddles.

118. The method of claim 114 wherein fixing the first member to a stationary object further comprises actuating a plurality of joints in the arm.

119. The method of claim 118 wherein actuating the joints in the arm comprises locking the plurality of joints in a desired position.

120. The method of claim 118 wherein the joints are actuated remotely from the first and second paddles.

121. The method of claim 114 wherein the stationary object is a retractor.

122. The method of claim 114 wherein the stationary object is a surgical table.

123. A method of immobilizing tissue of a moving surface of a beating heart while the heart continues beating during open or closed chest cardiac surgery comprising:

accessing the surface of the beating heart;

positioning a first member having at least one primary suction port along a first planar surface on the surface of the beating heart;

coupling a first suction source to at least one primary suction port of the first member;

creating a suction with the first suction source, the created suction then communicated to at least one primary suction port;

grasping the surface of the beating heart with the suction in at least one primary suction port; and fixing the position of the first member along the surface of the beating heart by a rigid attachment of the first member to a stationary object as the heart continues beating.

124. The method of claim 123 in which the step of accessing a surface of the beating heart comprises providing access through an intercostal space.

125. The method of claim 123 in which the step of accessing a surface of the beating heart comprises inserting an endoscope and a cutting instrument through the chest wall and cutting through the pericardium with the cutting instrument.

126. The method of claim 123 in which the step of positioning a first member having a first suction port along a first planar surface on the surface of the beating heart further comprises the steps of providing a first member having a first semicircular arm, the first semicircular arm having the first suction port disposed along a first planar surface of the first semicircular arm.

127. The method of claim 123 in which the step of positioning a first member having a first suction port along a first planar surface on the surface of the beating heart further comprises the steps of providing a first member having a first semicircular arm and a second semicircular arm, the second semicircular arm being disposed opposite the first semicircular arm to form a substantially circular area between the semicircular arms.

128. The method of claim 123 further comprising the steps of:

positioning a second member having a second suction port along a second planar surface on the surface of the beating heart;

coupling the first suction source or another suction source to the suction port of the second member;

grasping the surface of the beating heart with the suction in the second suction port; and fixing the position of the second member along the surface of the beating heart by a rigid attachment of the second member to a stationary object as the heart continues beating.

129. The method of claim 128 further comprising the steps of moving the first member away from the second member while maintaining the first member and the second member in grasping contact with the surface of the beating heart.

130. The method of claim 123 wherein fixing the position of the first member comprises actuating at least one joint in the arm.

131. The method of claim 130 wherein actuating the joint in the arm further comprises locking the joint.

132. The method of claim 130 wherein the joint is actuated remotely from the first member.

133. The method of claim 123 wherein fixing the position of the first member comprises actuating a plurality of joints in an arm.

134. The method of claim 133 wherein the joints are actuated remotely from the first member.

135. The method of claim 123 wherein the stationary object is a retractor.

136. The method of claim 135 further comprising using the retractor to access the surface of the beating heart.

137. The method of claim 123 wherein the stationary object is a surgical table.

* * * * *